United States Patent
Nobles

(10) Patent No.: US 11,839,370 B2
(45) Date of Patent: Dec. 12, 2023

(54) SUTURING DEVICES AND METHODS FOR SUTURING AN OPENING IN THE APEX OF THE HEART

(71) Applicant: HeartStitch, Inc., Fountain Valley, CA (US)

(72) Inventor: Anthony A. Nobles, St. Thomas, VI (US)

(73) Assignee: HeartStitch, Inc., Fountain Valley, CA (US)

( * ) Notice: Subject to any disclaimer, the term of this patent is extended or adjusted under 35 U.S.C. 154(b) by 425 days.

(21) Appl. No.: 16/624,611

(22) PCT Filed: Jun. 19, 2018

(86) PCT No.: PCT/US2018/038215
§ 371 (c)(1),
(2) Date: Dec. 19, 2019

(87) PCT Pub. No.: WO2018/236822
PCT Pub. Date: Dec. 27, 2018

(65) Prior Publication Data
US 2020/0214694 A1 Jul. 9, 2020

Related U.S. Application Data

(60) Provisional application No. 62/522,029, filed on Jun. 19, 2017.

(51) Int. Cl.
*A61B 17/04* (2006.01)
*A61B 17/00* (2006.01)

(52) U.S. Cl.
CPC ...... *A61B 17/0469* (2013.01); *A61B 17/0482* (2013.01); *A61B 2017/00243* (2013.01);
(Continued)

(58) Field of Classification Search
CPC ............ A61B 17/0469; A61B 17/0482; A61B 2017/00243; A61B 2017/00663;
(Continued)

(56) References Cited

U.S. PATENT DOCUMENTS

| 118,683 A | 9/1871 | Bruce |
| 1,064,307 A | 6/1913 | Fleming |

(Continued)

FOREIGN PATENT DOCUMENTS

| AU | 2006251579 | 11/2006 |
| CN | 101495049 | 12/2010 |

(Continued)

OTHER PUBLICATIONS

Advances in Vascular Surgery, by John S. Najarian, M.D. and John p. Delaney, M.D., copyright 1983 by Year Book Publishers, Inc. at pp. 94,95,96, and 224.

(Continued)

*Primary Examiner* — Darwin P Erezo
*Assistant Examiner* — Christian D Knauss
(74) *Attorney, Agent, or Firm* — Knobbe, Martens, Olson & Bear LLP

(57) ABSTRACT

Apparatuses and methods for closing a transapical opening (9) in a wall of the heart include utilizing a suturing device (100) that is advanced through the transapical opening (9), extending suture arms (110) from a retracted position to an extended position within a ventricle of the heart, extending needles (120) from a retracted position to an extended position through the wall of the heart to engage a plurality of suture portions (52) held by the suture arms (110), retracting the needles through the wall of the heart to draw the suture portions through the wall of the heart, retracting the suture arms, withdrawing the suturing device from the transapical opening, and closing the transapical opening (Continued)

with the suture portions (52). The needles (120) can be deployed from within the transapical opening (9) at an angle to a longitudinal axis of the suturing device or through the exterior wall of the heart parallel to the longitudinal axis of the suturing device.

18 Claims, 21 Drawing Sheets

(52) U.S. Cl.
CPC .............. *A61B 2017/00663* (2013.01); *A61B 2017/0472* (2013.01)

(58) Field of Classification Search
CPC ........ A61B 2017/0472; A61B 17/0057; A61B 2017/00575; A61B 2017/00637
See application file for complete search history.

(56) References Cited

U.S. PATENT DOCUMENTS

| | | |
|---|---|---|
| 1,822,330 A | 9/1931 | Ainslie |
| 1,989,919 A | 2/1935 | Everitt |
| 2,348,218 A | 5/1944 | Karle |
| 2,473,742 A | 6/1949 | Auzin |
| 2,548,602 A | 4/1951 | Greenburg |
| 2,637,290 A | 5/1953 | Sigoda |
| 2,738,790 A | 3/1956 | Todt, Sr. et al. |
| 2,849,002 A | 8/1958 | Oddo |
| 2,945,460 A | 7/1960 | Kagiyama |
| 3,241,554 A | 3/1966 | Coanda |
| 3,292,627 A | 12/1966 | Harautuneian |
| 3,394,705 A | 7/1968 | Abramson |
| 3,664,345 A | 5/1972 | Dabbs et al. |
| 3,665,926 A | 5/1972 | Flores |
| 3,774,596 A | 11/1973 | Cook |
| 3,828,790 A | 8/1974 | Curtiss et al. |
| 3,831,587 A | 8/1974 | Boyd |
| 3,842,840 A | 10/1974 | Schweizer |
| 3,877,434 A | 4/1975 | Ferguson et al. |
| 3,882,852 A | 5/1975 | Sinnreich |
| 3,882,855 A | 5/1975 | Schulte et al. |
| 3,888,117 A | 6/1975 | Lewis |
| 3,903,893 A | 9/1975 | Scheer |
| 3,946,740 A | 3/1976 | Bassett |
| 3,946,741 A | 3/1976 | Adair |
| 3,952,742 A | 4/1976 | Taylor |
| 3,976,079 A | 8/1976 | Samuels |
| 4,052,980 A | 10/1977 | Grams et al. |
| RE29,703 E | 7/1978 | Fatt |
| 4,107,953 A | 8/1978 | Casillo |
| 4,119,100 A | 10/1978 | Rickett |
| 4,164,225 A | 8/1979 | Johnson et al. |
| 4,230,119 A | 10/1980 | Blum |
| 4,291,698 A | 9/1981 | Fuchs et al. |
| 4,299,237 A | 11/1981 | Foti |
| 4,307,722 A | 12/1981 | Evans |
| 4,345,601 A | 8/1982 | Fukuda |
| 4,351,342 A | 9/1982 | Wiita et al. |
| 4,417,532 A | 11/1983 | Yasukata |
| 4,423,725 A | 1/1984 | Baran et al. |
| 4,447,227 A | 5/1984 | Kotsanis |
| 4,457,300 A | 7/1984 | Budde |
| 4,484,580 A | 11/1984 | Nomoto et al. |
| 4,512,338 A | 4/1985 | Balko et al. |
| 4,546,759 A | 10/1985 | Solar |
| 4,553,543 A | 11/1985 | Amarasinghe |
| 4,573,966 A | 3/1986 | Weikl et al. |
| 4,589,868 A | 5/1986 | Dretler |
| 4,610,662 A | 9/1986 | Weikl et al. |
| 4,617,738 A | 10/1986 | Kopacz |
| 4,662,068 A | 5/1987 | Polonsky |
| 4,664,114 A | 5/1987 | Ghodsian |
| 4,734,094 A | 3/1988 | Jacob et al. |
| 4,744,364 A | 5/1988 | Kensey |
| 4,750,492 A | 6/1988 | Jacobs |
| 4,771,776 A | 9/1988 | Powell et al. |
| 4,774,091 A | 9/1988 | Yamahira et al. |
| 4,794,928 A | 1/1989 | Kletschka |
| 4,795,427 A | 1/1989 | Helzel |
| 4,796,629 A | 1/1989 | Grayzel |
| 4,824,436 A | 4/1989 | Wolinsky |
| 4,827,931 A | 5/1989 | Longmore |
| 4,841,888 A | 6/1989 | Mills et al. |
| 4,861,330 A | 8/1989 | Voss |
| 4,898,168 A | 2/1990 | Yule |
| 4,923,461 A | 5/1990 | Caspari et al. |
| 4,926,860 A | 5/1990 | Stice et al. |
| 4,932,956 A | 6/1990 | Reddy et al. |
| 4,935,027 A | 6/1990 | Yoon |
| 4,954,126 A | 9/1990 | Wallsten |
| 4,957,498 A | 9/1990 | Caspari et al. |
| 4,972,845 A | 11/1990 | Iversen et al. |
| 4,981,149 A | 1/1991 | Yoon et al. |
| 4,983,116 A | 1/1991 | Koga |
| 4,984,564 A | 1/1991 | Yuen |
| 4,994,070 A | 2/1991 | Waters |
| 5,002,531 A | 3/1991 | Bonzel |
| 5,021,059 A | 6/1991 | Kensey et al. |
| 5,037,433 A | 8/1991 | Wilk et al. |
| 5,057,114 A | 10/1991 | Wittich et al. |
| 5,059,201 A | 10/1991 | Asnis |
| 5,065,772 A | 11/1991 | Cox, Jr. |
| 5,074,871 A | 12/1991 | Groshong |
| 5,078,743 A | 1/1992 | Mikalov et al. |
| 5,090,958 A | 2/1992 | Sahota |
| 5,100,418 A | 3/1992 | Yoon et al. |
| 5,104,394 A | 4/1992 | Knoepfler |
| 5,106,363 A | 4/1992 | Nobuyoshi |
| 5,108,416 A | 4/1992 | Ryan et al. |
| 5,108,419 A | 4/1992 | Reger et al. |
| 5,116,305 A | 5/1992 | Milder et al. |
| 5,122,122 A | 6/1992 | Allgood |
| 5,129,883 A | 7/1992 | Black |
| 5,133,724 A | 7/1992 | Wilson et al. |
| 5,135,484 A | 8/1992 | Wright |
| 5,160,339 A | 11/1992 | Chen et al. |
| 5,163,906 A | 11/1992 | Ahmadi |
| 5,167,223 A | 12/1992 | Koros et al. |
| 5,171,251 A | 12/1992 | Bregen et al. |
| 5,176,691 A | 1/1993 | Pierce |
| 5,192,301 A | 3/1993 | Kamiya et al. |
| 5,222,508 A | 6/1993 | Contarini |
| 5,222,941 A | 6/1993 | Don Michael |
| 5,222,974 A | 6/1993 | Kensey et al. |
| 5,224,948 A | 7/1993 | Abe et al. |
| 5,236,443 A | 8/1993 | Sontag |
| 5,242,459 A | 9/1993 | Buelna |
| 5,281,234 A | 1/1994 | Wilk et al. |
| 5,281,237 A | 1/1994 | Gimpelson |
| 5,282,827 A | 2/1994 | Kensey et al. |
| 5,286,259 A | 2/1994 | Ganguly et al. |
| 5,290,249 A | 3/1994 | Foster et al. |
| 5,291,639 A | 3/1994 | Baum et al. |
| 5,300,106 A | 4/1994 | Dahl et al. |
| 5,304,184 A | 4/1994 | Hathaway et al. |
| 5,308,323 A | 5/1994 | Sogawa et al. |
| 5,312,344 A | 5/1994 | Grinfeld |
| 5,314,409 A | 5/1994 | Sarosiek et al. |
| 5,320,604 A | 6/1994 | Walker et al. |
| 5,320,632 A | 6/1994 | Heidmueller |
| 5,330,446 A | 7/1994 | Weldon et al. |
| 5,330,497 A | 7/1994 | Freitas et al. |
| 5,331,975 A | 7/1994 | Bonutti |
| 5,336,229 A | 8/1994 | Noda |
| 5,336,231 A | 8/1994 | Adair |
| 5,337,736 A | 8/1994 | Reddy |
| 5,339,801 A | 8/1994 | Poloyko |
| 5,342,306 A | 8/1994 | Don Michael |
| 5,342,385 A | 8/1994 | Norelli et al. |
| 5,342,393 A | 8/1994 | Stack |
| 5,350,399 A | 9/1994 | Erlebacher et al. |
| 5,356,382 A | 10/1994 | Picha et al. |

(56) References Cited

U.S. PATENT DOCUMENTS

| | | |
|---|---|---|
| 5,364,407 A | 11/1994 | Poll |
| 5,364,408 A | 11/1994 | Gordon |
| 5,368,601 A | 11/1994 | Sauer et al. |
| 5,370,618 A | 12/1994 | Leonhardt |
| 5,370,685 A | 12/1994 | Stevens |
| 5,374,275 A | 12/1994 | Bradley et al. |
| 5,380,284 A | 1/1995 | Don Michael |
| 5,382,261 A | 1/1995 | Palmaz |
| 5,383,854 A | 1/1995 | Safar et al. |
| 5,383,896 A | 1/1995 | Gershony et al. |
| 5,383,897 A | 1/1995 | Wholey |
| 5,383,905 A | 1/1995 | Golds et al. |
| 5,389,103 A | 2/1995 | Melzer et al. |
| 5,391,147 A | 2/1995 | Imran et al. |
| 5,391,174 A | 2/1995 | Weston |
| 5,395,383 A | 3/1995 | Adams et al. |
| 5,397,325 A | 3/1995 | Badia et al. |
| 5,403,329 A | 4/1995 | Hinchcliffe |
| 5,403,331 A | 4/1995 | Chesterfield et al. |
| 5,403,341 A | 4/1995 | Solar |
| 5,405,322 A | 4/1995 | Lennox et al. |
| 5,405,354 A | 4/1995 | Sarrett |
| 5,417,699 A | 5/1995 | Klein et al. |
| 5,417,700 A | 5/1995 | Egan |
| 5,423,777 A | 6/1995 | Tajiri et al. |
| 5,423,837 A | 6/1995 | Mericle et al. |
| 5,425,708 A | 6/1995 | Nasu |
| 5,425,737 A | 6/1995 | Burbank et al. |
| 5,425,744 A | 6/1995 | Fagan et al. |
| 5,429,118 A | 7/1995 | Cole et al. |
| 5,431,666 A | 7/1995 | Sauer et al. |
| 5,439,470 A | 8/1995 | Li |
| 5,445,167 A | 8/1995 | Yoon et al. |
| 5,447,515 A | 9/1995 | Robicsek |
| 5,452,513 A | 9/1995 | Zinnbauer et al. |
| 5,454,823 A | 10/1995 | Richardson et al. |
| 5,458,574 A | 10/1995 | Machold et al. |
| 5,458,609 A | 10/1995 | Gordon et al. |
| 5,462,560 A | 10/1995 | Stevens |
| 5,462,561 A | 10/1995 | Voda |
| 5,470,338 A | 11/1995 | Whitefield et al. |
| 5,474,572 A | 12/1995 | Hayburst |
| 5,476,469 A | 12/1995 | Hathaway et al. |
| 5,476,470 A | 12/1995 | Fitzgibbons, Jr. |
| 5,496,332 A | 3/1996 | Sierra et al. |
| 5,499,991 A | 3/1996 | Garman et al. |
| 5,501,691 A | 3/1996 | Goldrath |
| 5,507,754 A | 4/1996 | Green et al. |
| 5,507,755 A | 4/1996 | Gresl et al. |
| 5,514,159 A | 5/1996 | Matula et al. |
| 5,520,609 A | 5/1996 | Moll et al. |
| 5,520,702 A | 5/1996 | Sauer et al. |
| 5,522,961 A | 6/1996 | Leonhardt |
| 5,527,321 A | 6/1996 | Hinchliffe |
| 5,527,322 A | 6/1996 | Klein et al. |
| 5,527,338 A | 6/1996 | Purdy |
| 5,540,658 A | 7/1996 | Evans et al. |
| 5,540,704 A | 7/1996 | Gordon et al. |
| 5,545,170 A | 8/1996 | Hart |
| 5,549,633 A | 8/1996 | Evans et al. |
| 5,558,642 A | 9/1996 | Schweich et al. |
| 5,558,644 A | 9/1996 | Boyd et al. |
| RE35,352 E | 10/1996 | Peters |
| 5,562,686 A | 10/1996 | Sauer et al. |
| 5,562,688 A | 10/1996 | Riza |
| 5,565,122 A | 10/1996 | Zinnbauer et al. |
| 5,571,090 A | 11/1996 | Sherts |
| 5,573,540 A | 11/1996 | Yoon |
| 5,584,835 A | 12/1996 | Greenfield |
| 5,584,861 A | 12/1996 | Swain et al. |
| 5,591,195 A | 1/1997 | Taheri et al. |
| 5,593,422 A | 1/1997 | Muijs Van de Moer et al. |
| 5,599,307 A | 2/1997 | Bacher et al. |
| 5,603,718 A | 2/1997 | Xu |
| 5,613,974 A | 3/1997 | Andreas et al. |
| 5,613,975 A | 3/1997 | Christy |
| 5,626,590 A | 5/1997 | Wilk |
| 5,630,833 A | 5/1997 | Katsaros et al. |
| 5,632,751 A | 5/1997 | Piraka |
| 5,632,752 A | 5/1997 | Buelna |
| 5,634,936 A | 6/1997 | Linden et al. |
| 5,637,097 A | 6/1997 | Yoon |
| 5,643,289 A | 7/1997 | Sauer et al. |
| 5,645,553 A | 7/1997 | Kolesa et al. |
| 5,662,663 A | 9/1997 | Shallman |
| 5,669,917 A | 9/1997 | Sauer et al. |
| 5,669,971 A | 9/1997 | Bok et al. |
| 5,674,198 A | 10/1997 | Leone |
| 5,681,296 A | 10/1997 | Ishida |
| 5,681,351 A | 10/1997 | Jamiolkowski et al. |
| 5,688,245 A | 11/1997 | Runge |
| 5,690,674 A | 11/1997 | Diaz |
| 5,695,468 A | 12/1997 | Lafontaine et al. |
| 5,695,504 A | 12/1997 | Gifford, III et al. |
| 5,697,905 A | 12/1997 | D'Amnbrosio |
| 5,700,273 A | 12/1997 | Buelna et al. |
| 5,700,277 A | 12/1997 | Nash et al. |
| 5,707,379 A | 1/1998 | Fleenor et al. |
| 5,709,693 A | 1/1998 | Taylor |
| 5,716,329 A | 2/1998 | Dieter |
| 5,720,757 A | 2/1998 | Hathaway et al. |
| 5,722,983 A | 3/1998 | Van Der Weegen |
| 5,728,109 A | 3/1998 | Schulze et al. |
| 5,738,629 A | 4/1998 | Moll et al. |
| 5,743,852 A | 4/1998 | Johnson |
| 5,746,753 A | 5/1998 | Sullivan et al. |
| 5,749,883 A | 5/1998 | Halpern |
| 5,759,188 A | 6/1998 | Yoon |
| 5,766,183 A | 6/1998 | Sauer |
| 5,766,220 A | 6/1998 | Moenning |
| 5,769,870 A | 6/1998 | Salahieh et al. |
| 5,779,719 A | 7/1998 | Klein et al. |
| 5,792,152 A | 8/1998 | Klein et al. |
| 5,792,153 A | 8/1998 | Swain et al. |
| 5,795,289 A | 8/1998 | Wyttenbach |
| 5,795,325 A | 8/1998 | Valley et al. |
| 5,797,948 A | 8/1998 | Dunham |
| 5,797,960 A | 8/1998 | Stevens et al. |
| 5,810,757 A | 9/1998 | Sweezer et al. |
| 5,810,849 A | 9/1998 | Kontos |
| 5,810,850 A | 9/1998 | Hathaway et al. |
| 5,817,108 A | 10/1998 | Poncet |
| 5,817,110 A | 10/1998 | Kronner |
| 5,820,631 A | 10/1998 | Nobles |
| 5,836,955 A | 11/1998 | Buelna et al. |
| 5,843,100 A | 12/1998 | Meade |
| 5,846,251 A | 12/1998 | Hart |
| 5,846,253 A | 12/1998 | Buelna et al. |
| 5,853,399 A | 12/1998 | Sasaki |
| 5,853,422 A | 12/1998 | Huebsch et al. |
| 5,855,585 A | 1/1999 | Kontos |
| 5,860,990 A | 1/1999 | Nobles et al. |
| 5,860,991 A | 1/1999 | Klein et al. |
| 5,860,992 A | 1/1999 | Daniel et al. |
| 5,860,997 A | 1/1999 | Bonutti |
| 5,861,003 A | 1/1999 | Latson et al. |
| 5,865,729 A | 2/1999 | Meehan et al. |
| 5,868,708 A | 2/1999 | Hart et al. |
| 5,868,762 A | 2/1999 | Cragg et al. |
| 5,871,320 A | 2/1999 | Kovac |
| 5,871,537 A | 2/1999 | Holman et al. |
| 5,876,411 A | 3/1999 | Kontos |
| 5,899,921 A | 5/1999 | Caspari et al. |
| 5,902,311 A | 5/1999 | Andreas et al. |
| 5,902,321 A | 5/1999 | Caspari et al. |
| 5,906,577 A | 5/1999 | Beane et al. |
| 5,908,428 A | 6/1999 | Scirica et al. |
| 5,919,200 A | 7/1999 | Stambaugh et al. |
| 5,919,208 A | 7/1999 | Valenti |
| 5,928,192 A | 7/1999 | Maahs |
| 5,931,844 A | 8/1999 | Thompson et al. |
| 5,935,098 A | 8/1999 | Blaisdell et al. |
| 5,935,149 A | 8/1999 | Ek |
| 5,944,730 A | 8/1999 | Nobles et al. |

(56) References Cited

U.S. PATENT DOCUMENTS

| | | |
|---|---|---|
| 5,951,588 A | 9/1999 | Moenning |
| 5,951,590 A | 9/1999 | Goldfarb |
| 5,954,732 A | 9/1999 | Hart et al. |
| 5,967,970 A | 10/1999 | Cowan et al. |
| 5,971,983 A | 10/1999 | Lesh |
| 5,972,005 A | 10/1999 | Stalker et al. |
| 5,980,539 A | 11/1999 | Kontos |
| 5,993,466 A | 11/1999 | Yoon |
| 5,997,555 A | 12/1999 | Kontos |
| 6,001,109 A | 12/1999 | Kontos |
| 6,004,337 A | 12/1999 | Kieturakis et al. |
| 6,010,530 A | 1/2000 | Goicoechea |
| 6,015,428 A | 1/2000 | Pagedas |
| 6,024,747 A | 2/2000 | Kontos |
| 6,033,430 A | 3/2000 | Bonutti |
| 6,036,699 A | 3/2000 | Andreas et al. |
| 6,059,800 A | 5/2000 | Hart et al. |
| 6,066,160 A | 5/2000 | Colvin et al. |
| 6,068,648 A | 5/2000 | Cole et al. |
| 6,071,271 A | 6/2000 | Baker et al. |
| 6,077,277 A | 6/2000 | Mollenauer et al. |
| 6,086,608 A | 7/2000 | Ek et al. |
| 6,099,553 A | 8/2000 | Hart et al. |
| 6,110,185 A | 8/2000 | Barra et al. |
| 6,113,580 A | 9/2000 | Dolisi |
| 6,117,144 A | 9/2000 | Nobles et al. |
| 6,126,677 A | 10/2000 | Ganaja et al. |
| 6,136,010 A | 10/2000 | Modesitt et al. |
| 6,143,015 A | 11/2000 | Nobles |
| 6,159,234 A | 12/2000 | Bonutti et al. |
| 6,171,319 B1 | 1/2001 | Nobles et al. |
| 6,174,324 B1 | 1/2001 | Egan et al. |
| 6,187,026 B1 | 2/2001 | Devlin et al. |
| 6,190,396 B1 | 2/2001 | Whitin et al. |
| 6,200,329 B1 | 3/2001 | Fung et al. |
| 6,203,565 B1 | 3/2001 | Bonutti et al. |
| 6,210,429 B1 | 4/2001 | Vardi et al. |
| 6,217,591 B1 | 4/2001 | Egan et al. |
| 6,241,699 B1 | 6/2001 | Suresh et al. |
| 6,245,079 B1 | 6/2001 | Nobles et al. |
| 6,245,080 B1 | 6/2001 | Levinson |
| 6,248,121 B1 | 6/2001 | Nobles |
| 6,280,460 B1 | 8/2001 | Bolduc et al. |
| 6,290,674 B1 | 9/2001 | Roue et al. |
| 6,332,889 B1 | 12/2001 | Sancoff et al. |
| 6,348,059 B1 | 2/2002 | Hathaway et al. |
| 6,352,543 B1 | 3/2002 | Cole et al. |
| 6,383,208 B1 | 5/2002 | Sancoff et al. |
| 6,395,015 B1 | 5/2002 | Borst et al. |
| 6,409,739 B1 | 6/2002 | Nobles et al. |
| 6,432,115 B1 | 8/2002 | Mollenauer et al. |
| 6,468,293 B2 | 10/2002 | Bonutti et al. |
| 6,508,777 B1 | 1/2003 | Macoviak et al. |
| 6,527,785 B2 | 3/2003 | Sancoff et al. |
| 6,533,795 B1 | 3/2003 | Tran et al. |
| 6,537,299 B1 | 3/2003 | Hogendijk et al. |
| 6,547,725 B1 | 4/2003 | Paolitto et al. |
| 6,547,760 B1 | 4/2003 | Samson et al. |
| 6,551,331 B2 | 4/2003 | Nobles et al. |
| 6,562,052 B2 | 5/2003 | Nobles et al. |
| 6,585,689 B1 | 7/2003 | Macoviak et al. |
| 6,663,643 B2 | 12/2003 | Field et al. |
| 6,679,895 B1 | 1/2004 | Sancoff et al. |
| 6,682,540 B1 | 1/2004 | Sancoff et al. |
| 6,716,243 B1 | 4/2004 | Colvin et al. |
| 6,726,651 B1 | 4/2004 | Robinson et al. |
| 6,733,509 B2 | 5/2004 | Nobles et al. |
| 6,767,352 B2 | 7/2004 | Field et al. |
| 6,770,076 B2 | 8/2004 | Foerster |
| 6,770,084 B1 | 8/2004 | Bain et al. |
| 6,786,913 B1 | 9/2004 | Sancoff |
| 6,978,176 B2 | 1/2005 | Lattouf |
| 6,855,157 B2 | 2/2005 | Foerster et al. |
| 6,893,448 B2 | 5/2005 | O'Quinn et al. |
| 6,911,034 B2 | 6/2005 | Nobles et al. |
| 6,913,600 B2 | 7/2005 | Valley et al. |
| 6,936,057 B1 | 8/2005 | Nobles |
| 7,004,952 B2 | 2/2006 | Nobles et al. |
| 7,083,630 B2 | 8/2006 | DeVries et al. |
| 7,083,638 B2 | 8/2006 | Foerster |
| 7,090,686 B2 | 8/2006 | Nobles et al. |
| 7,090,690 B2 | 8/2006 | Foerster et al. |
| 7,118,583 B2 | 10/2006 | O'Quinn et al. |
| 7,160,309 B2 | 1/2007 | Voss |
| 7,172,595 B1 | 2/2007 | Goble |
| 7,220,266 B2 | 5/2007 | Gambale |
| 7,232,446 B1 | 6/2007 | Farris |
| 7,235,086 B2 | 6/2007 | Sauer et al. |
| 7,326,221 B2 | 2/2008 | Sakamoto et al. |
| 7,329,272 B2 | 2/2008 | Burkhart et al. |
| 7,338,502 B2 | 3/2008 | Rosenblatt |
| 7,381,210 B2 | 6/2008 | Zarbatany et al. |
| 7,399,304 B2 | 7/2008 | Gambale et al. |
| 7,435,251 B2 | 10/2008 | Green |
| 7,449,024 B2 | 11/2008 | Stafford |
| 7,491,217 B1 | 2/2009 | Hendren |
| 7,601,161 B1 | 10/2009 | Nobles et al. |
| 7,628,797 B2 | 12/2009 | Tieu et al. |
| 7,635,386 B1 | 12/2009 | Gammie |
| 7,637,926 B2 | 12/2009 | Foerster et al. |
| 7,722,629 B2 | 5/2010 | Chambers |
| 7,803,167 B2 | 9/2010 | Nobles et al. |
| 7,842,051 B2 | 11/2010 | Dana et al. |
| 7,846,181 B2 | 12/2010 | Schwartz et al. |
| 7,879,072 B2 | 2/2011 | Bonutti et al. |
| 7,905,892 B2 | 3/2011 | Nobles et al. |
| 7,918,867 B2 | 4/2011 | Dana et al. |
| 7,931,641 B2 | 4/2011 | Chang et al. |
| 7,993,368 B2 | 8/2011 | Gambale et al. |
| 8,075,573 B2 | 12/2011 | Gambale et al. |
| 8,083,754 B2 | 12/2011 | Pantages et al. |
| 8,105,355 B2 | 1/2012 | Page et al. |
| 8,197,497 B2 | 6/2012 | Nobles et al. |
| 8,202,281 B2 | 6/2012 | Voss |
| 8,246,636 B2 | 8/2012 | Nobles et al. |
| 8,252,005 B2 | 8/2012 | Findlay, III et al. |
| 8,282,659 B2 | 10/2012 | Oren et al. |
| 8,287,556 B2 | 10/2012 | Gilkey et al. |
| 8,298,291 B2 | 10/2012 | Ewers et al. |
| 8,303,622 B2 | 11/2012 | Alkhatib |
| 8,348,962 B2 | 1/2013 | Nobles et al. |
| 8,372,089 B2 | 2/2013 | Nobles et al. |
| 8,398,676 B2 | 3/2013 | Roorda et al. |
| 8,430,893 B2 | 4/2013 | Ma |
| 8,469,975 B2 | 6/2013 | Nobles et al. |
| 8,496,676 B2 | 7/2013 | Nobles et al. |
| 8,500,776 B2 | 8/2013 | Ebner |
| 8,540,736 B2 | 9/2013 | Gaynor et al. |
| 8,568,427 B2 | 10/2013 | Nobles et al. |
| 8,623,036 B2 | 1/2014 | Harrison et al. |
| 8,728,105 B2 | 5/2014 | Aguirre |
| 8,758,370 B2 | 6/2014 | Shikhman et al. |
| 8,771,296 B2 | 7/2014 | Nobles et al. |
| 9,131,938 B2 | 9/2015 | Nobles et al. |
| 9,326,764 B2 | 5/2016 | Nobles et al. |
| 9,332,976 B2 | 5/2016 | Yribarren |
| 9,364,238 B2 | 6/2016 | Bakos et al. |
| 9,398,907 B2 | 7/2016 | Nobles et al. |
| 9,402,605 B2 | 8/2016 | Viola |
| 9,649,106 B2 | 5/2017 | Nobles et al. |
| 9,706,988 B2 | 7/2017 | Nobles et al. |
| 10,178,993 B2 | 1/2019 | Nobles et al. |
| 10,182,802 B2 | 1/2019 | Nobles et al. |
| 10,194,902 B2 | 2/2019 | Nobles et al. |
| 10,285,687 B2 | 5/2019 | Nobles et al. |
| 10,420,545 B2 | 9/2019 | Nobles et al. |
| 10,512,458 B2 | 12/2019 | Nobles |
| 10,610,216 B2 | 4/2020 | Nobles et al. |
| 10,624,629 B2 | 4/2020 | Nobles et al. |
| 2001/0031973 A1 | 10/2001 | Nobles et al. |
| 2002/0013601 A1 | 1/2002 | Nobles et al. |
| 2002/0045908 A1 | 4/2002 | Nobles et al. |
| 2002/0049453 A1* | 4/2002 | Nobles ............... A61B 17/0057 606/139 |

(56) References Cited

U.S. PATENT DOCUMENTS

| | | |
|---|---|---|
| 2002/0096183 A1 | 7/2002 | Stevens et al. |
| 2002/0128598 A1 | 9/2002 | Nobles |
| 2002/0169475 A1 | 11/2002 | Gainor et al. |
| 2002/0183787 A1 | 12/2002 | Wahr et al. |
| 2003/0078601 A1 | 4/2003 | Skikhman et al. |
| 2003/0114863 A1 | 6/2003 | Field et al. |
| 2003/0144673 A1 | 7/2003 | Onuki et al. |
| 2003/0204205 A1 | 10/2003 | Sauer et al. |
| 2003/0208209 A1 | 11/2003 | Gambale et al. |
| 2003/0220667 A1 | 11/2003 | van der Burg et al. |
| 2004/0015177 A1 | 1/2004 | Chu |
| 2004/0044365 A1 | 3/2004 | Bachman |
| 2004/0059351 A1 | 3/2004 | Eigler et al. |
| 2004/0102797 A1 | 5/2004 | Golden et al. |
| 2004/0153116 A1 | 8/2004 | Nobles |
| 2004/0236356 A1 | 11/2004 | Rioux et al. |
| 2004/0260298 A1 | 12/2004 | Kaiseer et al. |
| 2005/0033361 A1 | 2/2005 | Galdonik et al. |
| 2005/0070923 A1 | 3/2005 | McIntosh |
| 2005/0149066 A1 | 7/2005 | Stafford |
| 2005/0187575 A1 | 8/2005 | Hallbeck et al. |
| 2005/0203564 A1 | 9/2005 | Nobles |
| 2005/0228407 A1 | 10/2005 | Nobles et al. |
| 2005/0261708 A1 | 11/2005 | Pasricha et al. |
| 2005/0261710 A1 | 11/2005 | Sakamoto et al. |
| 2005/0277986 A1 | 12/2005 | Foerster et al. |
| 2006/0052813 A1 | 3/2006 | Nobles |
| 2006/0064113 A1 | 3/2006 | Nakao |
| 2006/0064115 A1 | 3/2006 | Allen et al. |
| 2006/0069397 A1 | 3/2006 | Nobles et al. |
| 2006/0074484 A1 | 4/2006 | Huber |
| 2006/0095052 A1 | 5/2006 | Chambers |
| 2006/0195120 A1 | 8/2006 | Nobles et al. |
| 2006/0248691 A1 | 11/2006 | Rosemann |
| 2006/0265010 A1 | 11/2006 | Paraschac et al. |
| 2006/0282088 A1 | 12/2006 | Ryan |
| 2006/0282094 A1 | 12/2006 | Stokes et al. |
| 2006/0282102 A1 | 12/2006 | Nobles et al. |
| 2006/0287657 A1 | 12/2006 | Bachman |
| 2007/0005079 A1 | 1/2007 | Zarbatany et al. |
| 2007/0010829 A1 | 1/2007 | Nobles et al. |
| 2007/0043385 A1 | 2/2007 | Nobles et al. |
| 2007/0060930 A1 | 3/2007 | Hamilton et al. |
| 2007/0106310 A1 | 5/2007 | Goldin et al. |
| 2007/0118151 A1 | 5/2007 | Davidson |
| 2007/0142846 A1 | 6/2007 | Catanese, III et al. |
| 2007/0213757 A1 | 9/2007 | Boraiah |
| 2007/0219630 A1 | 9/2007 | Chu |
| 2007/0276413 A1 | 11/2007 | Nobles |
| 2007/0276414 A1 | 11/2007 | Nobles |
| 2008/0033459 A1 | 2/2008 | Shafi et al. |
| 2008/0065145 A1 | 3/2008 | Carpenter |
| 2008/0077162 A1 | 3/2008 | Domingo |
| 2008/0114384 A1 | 5/2008 | Chang et al. |
| 2008/0188873 A1 | 8/2008 | Speziali |
| 2008/0228201 A1 | 9/2008 | Zarbatany |
| 2008/0269786 A1 | 10/2008 | Nobles et al. |
| 2008/0269788 A1 | 10/2008 | Phillips |
| 2009/0036906 A1 | 2/2009 | Stafford |
| 2009/0048615 A1 | 2/2009 | McIntosh |
| 2009/0099410 A1 | 4/2009 | De Marchena |
| 2009/0105729 A1 | 4/2009 | Zentgraf |
| 2009/0105751 A1 | 4/2009 | Zentgraf |
| 2009/0118726 A1 | 5/2009 | Auth et al. |
| 2009/0125042 A1 | 5/2009 | Mouw |
| 2009/0287183 A1 | 11/2009 | Bishop et al. |
| 2009/0299409 A1 | 12/2009 | Coe et al. |
| 2009/0312772 A1 | 12/2009 | Chu |
| 2009/0312783 A1 | 12/2009 | Whayne et al. |
| 2009/0312789 A1 | 12/2009 | Kassab et al. |
| 2010/0016870 A1 | 1/2010 | Campbell |
| 2010/0030242 A1 | 2/2010 | Nobles et al. |
| 2010/0042147 A1 | 2/2010 | Janovsky et al. |
| 2010/0063586 A1 | 3/2010 | Hasenkam et al. |
| 2010/0087838 A1 | 4/2010 | Nobles et al. |
| 2010/0094314 A1 | 4/2010 | Hernlund et al. |
| 2010/0100167 A1 | 4/2010 | Bortlein et al. |
| 2010/0179585 A1 | 7/2010 | Carpenter et al. |
| 2010/0210899 A1 | 8/2010 | Schankereli |
| 2011/0190793 A1* | 8/2011 | Nobles .............. A61B 17/0469 606/144 |
| 2011/0202077 A1 | 8/2011 | Chin et al. |
| 2011/0224720 A1 | 9/2011 | Kassab et al. |
| 2011/0251627 A1 | 10/2011 | Hamilton et al. |
| 2012/0016384 A1 | 1/2012 | Wilke et al. |
| 2012/0035628 A1 | 2/2012 | Aguirre et al. |
| 2012/0059398 A1 | 3/2012 | Pate et al. |
| 2012/0143222 A1 | 6/2012 | Dravis et al. |
| 2012/0165838 A1 | 6/2012 | Kobylewski et al. |
| 2012/0296373 A1 | 11/2012 | Roorda et al. |
| 2013/0103056 A1 | 4/2013 | Chu |
| 2013/0261645 A1 | 10/2013 | Nobles et al. |
| 2013/0324800 A1 | 12/2013 | Cahill |
| 2014/0276975 A1* | 9/2014 | Argentine .......... A61B 17/0057 606/144 |
| 2014/0309670 A1 | 10/2014 | Bakos et al. |
| 2014/0379006 A1 | 12/2014 | Sutherland et al. |
| 2015/0126815 A1 | 5/2015 | Nobles |
| 2015/0359531 A1 | 12/2015 | Sauer |
| 2016/0151064 A1 | 6/2016 | Nobles |
| 2017/0035425 A1 | 2/2017 | Fegelman et al. |
| 2017/0049451 A1 | 2/2017 | Hausen |
| 2017/0296168 A1 | 4/2017 | Nobles et al. |
| 2017/0128059 A1 | 5/2017 | Coe et al. |
| 2019/0029672 A1 | 1/2019 | Nobles et al. |
| 2019/0150903 A1 | 5/2019 | Nobles |
| 2019/0239880 A1 | 8/2019 | Nobles |

FOREIGN PATENT DOCUMENTS

| | | |
|---|---|---|
| CN | 101257852 | 8/2011 |
| CN | ZL 201280029608.6 | 10/2016 |
| DE | 29 01 701 | 7/1980 |
| EP | 0 241 038 | 10/1987 |
| EP | 0 544 485 | 6/1993 |
| EP | 0839 550 | 5/1998 |
| EP | 0 894 475 | 2/1999 |
| EP | 1 196 093 | 4/2002 |
| EP | 1 303 218 | 4/2003 |
| EP | 0 941 698 | 5/2005 |
| EP | 0 983 027 | 12/2005 |
| EP | 1 852 071 | 11/2007 |
| EP | 1 987 779 | 11/2008 |
| EP | 2 572 649 | 3/2013 |
| FR | 2 701 401 | 8/1994 |
| JP | A 9507398 | 7/1997 |
| JP | 09-266910 A | 10/1997 |
| JP | H10-43192 | 2/1998 |
| JP | 2001-524864 | 12/2001 |
| JP | 2003-139113 A2 | 5/2003 |
| JP | 2003-225241 A | 8/2003 |
| JP | 2007-503870 | 3/2007 |
| JP | 2008-514305 | 5/2008 |
| JP | 2008-541857 | 11/2008 |
| JP | 2008-546454 | 12/2008 |
| JP | 2009-261960 | 11/2009 |
| JP | 2010-522625 | 7/2010 |
| JP | 2011-067251 | 4/2011 |
| JP | 5848125 | 12/2015 |
| RU | 2010 125954 | 1/2012 |
| SU | 1560129 A1 | 4/1990 |
| WO | WO 92/05828 | 4/1992 |
| WO | WO 93/01750 | 2/1993 |
| WO | WO 93/07800 | 4/1993 |
| WO | WO 95/12429 | 5/1995 |
| WO | WO 95/17127 | 6/1995 |
| WO | WO 95/25468 | 9/1995 |
| WO | WO 95/25470 | 9/1995 |
| WO | WO 96/03083 | 2/1996 |
| WO | WO 96/29012 | 9/1996 |
| WO | WO 96/40347 | 12/1996 |
| WO | WO 97/03613 | 2/1997 |
| WO | WO 97/47261 | 2/1997 |
| WO | WO 97/07745 | 3/1997 |

(56) References Cited

FOREIGN PATENT DOCUMENTS

| | | |
|---|---|---|
| WO | WO 97/12540 | 4/1997 |
| WO | WO 97/20505 | 6/1997 |
| WO | WO 97/24975 | 7/1997 |
| WO | WO 97/27807 | 8/1997 |
| WO | WO 97/40738 | 11/1997 |
| WO | WO 98/12970 | 4/1998 |
| WO | WO 98/52476 | 11/1998 |
| WO | WO 99/40851 | 8/1999 |
| WO | WO 99/42160 | 8/1999 |
| WO | WO 99/45848 | 9/1999 |
| WO | WO 00/002489 | 1/2000 |
| WO | WO 01/001868 | 1/2001 |
| WO | WO 01/95809 | 12/2001 |
| WO | WO 02/024078 | 3/2002 |
| WO | WO 04/012789 | 2/2004 |
| WO | WO 04/096013 | 11/2004 |
| WO | WO 06/127636 | 11/2006 |
| WO | WO 07/001936 | 1/2007 |
| WO | WO 07/016261 | 2/2007 |
| WO | WO 08/121738 | 10/2008 |
| WO | WO 09/081396 | 7/2009 |
| WO | WO 09/137766 | 11/2009 |
| WO | WO 11/094619 | 8/2011 |
| WO | WO 11/137224 | 11/2011 |
| WO | WO 11/156782 | 12/2011 |
| WO | WO 12/012336 | 1/2012 |
| WO | WO 12/142338 | 10/2012 |
| WO | WO 13/027209 | 2/2013 |
| WO | WO 13/142487 | 9/2013 |
| WO | WO 13/170081 | 11/2013 |
| WO | WO 15/002815 | 1/2015 |
| WO | WO 15/085145 | 6/2015 |
| WO | WO 17/180092 | 10/2017 |
| WO | WO 19/035095 | 2/2019 |
| WO | WO 19/051379 | 3/2019 |
| WO | WO 19/055433 | 3/2019 |

OTHER PUBLICATIONS

Cardio Medical Solutions, Inc. brochure titled: "Baladi Inverter for Clamp less Surgery"—Undated.

Clinical Evaluation of Arteriovenous Fistulas as an Adjunct to Lower Extremity Arterial Reconstructions, by Herbert Dardick, M.D., in Current Critical Problems in Vascular Surgery, copyright 1989 by Quality Medical Publishing Inc., at p. 383.

Current Therapy in Vascular Surgery, 2nd edition, by Calvin B. Ernst, M.D. and James C. Stanley, M.D., copyright 1991 By B.C. Decker, Inc., at pp. A and 140.

Eskuri, A., The Design of a Minimally Invasive Vascular Suturing Device, Thesis submitted to Rose-Hulman Institute of Technology, Nov. 1999.

Manual of Vascular Surgery, vol. 2, Edwin J. Wylie, Ronald J. Stoney, William K. Ehrenfeld and David J. Effeney (Richard H. Egdahl ed.), copyright 1986 by Springer-Verlag New York Inc., at p. 41.

Nursing the Open-Heart Surgery Patient, By Mary Jo Aspinall, R.N., M.N., copyright 1973 by McGraw Hill, Inc., at pp. 216 and 231.

Operative Arterial Surgery, by P.R. Bell, M.D., and W Barrie, M.D., copyright 1981 by Bell, Barrie, and Leicester Royal Infirmary, printed byJohn Wright &Sons, pp. 16, 17, 104, 105, 112, and 113.

Sinus Venous Type of Atrial Septal Defect with Partial Anomalous Pulmonary Venous Return, by Francis Robicsek, MD., et ai, in Journal of Thoracic and Cardiovascular Surgery, Oct. 1979, vol. 78, No. 4, at pp. 559-562.

Techniques in Vascular Surgery, by Denton A. Cooley, MD. and Don C. Wukasch, MD., copyright 1979 by WB. Saunders Co., at pp. 38,57,86,134,156, and 184.

The problem: Closing wounds in deep areas during laparoscopic operations The solution: REMA Medizintechnik GmbH (no date).

Vascular Access, Principles and Practice, 3rd edition, by Samuel Eric Wilson, MD., copyright 1996, 1988, 1980 by Mosby-Year Book, Inc., pp. 89 and 159.

Vascular and Endovascular Surgery, by Jonathan D. Beard and Peter Gainers, copyright 1998 by W. B. Saunders Co., Ltd, p. 414.

Vascular Surgery, 3rd edition, vol. 1, by Robert B. Rutherford, MD., copyright 1989, 1984, 1976 By W. B.SaundersCo., at pp. 347, 348, 354, 594, 607, 622, 675, 677, 680, 698, 700, 721, 727, 735, and 829.

Vascular Surgery, 4th edition by Robert B. Rutherford, MD., copyright 1995,1989,1976, by W.B. Saunders Co., vol. 1, at pp. 400-404, 661, and A.

Vascular Surgery, 4th edition, by Robert B. Rutherford, M.D., copyright 1995, 1989, 1984, 1976 by W. B. Saunders Co., vol. 2, at pp. 1318, 1363, 1426, 1564, and 1580.

Vascular Surgery, by Robert B. Rutherford, M.D. copyright1977 by WB. Saunders Co., at pp. 334 and 817.

International Search Report and Written Opinion of PCT/US2018/038215, dated Sep. 25, 2018.

International Preliminary Report on Patentability of PCT/US2018/038215, dated Dec. 24, 2019.

\* cited by examiner

SUTURING DEVICES AND METHODS FOR SUTURING AN OPENING IN THE APEX OF THE HEART

INCORPORATION BY REFERENCE TO ANY PRIORITY APPLICATIONS

This application is a U.S. national phase application of International Application No. PCT/US2018/038215, filed Jun. 9, 2018, which claims priority benefit of U.S. Provisional Application No. 62/522029, filed Jun. 19, 2017, the entirety of which is hereby incorporated by reference.

BACKGROUND

Field

Embodiments of the present invention relate to suturing devices and methods. Some embodiments relate to suturing devices and methods for suturing an anatomic structure, such as a heart.

Description of the Related Art

Health practitioners frequently use sutures to close various openings such as cuts, punctures, and incisions in various places in the human body. Generally, sutures are convenient to use and function properly to hold openings in biological tissue closed thereby aiding in blood clotting, healing, and prevention of scarring.

There are some circumstances under which it is not feasible to use conventional sutures and suturing methods to close an opening. Additionally, there are some circumstances under which the use of conventional sutures and suturing methods require invasive procedures that subject a patient to risk of infection, delays in recovery, increases in pain, and other complications.

SUMMARY

Methods, systems and apparatuses are provided in certain embodiments of the present application to suture an opening in the apex of the heart.

In one embodiment, a suturing device for closing a transapical opening extending through a wall of the heart between inner and outer surfaces of the heart is provided. The suturing device includes an elongate housing having a proximal end and a distal end configured to be delivered through the transapical opening into a chamber of the heart, a handle at the proximal end of the elongate housing configured to be manipulate from outside of the heart, a plurality of arms arranged about an outer diameter of an arm-receiving portion of the elongate housing, the arms being extendable from the arm-receiving portion from a retracted position within the arm-receiving portion to an extended position when the arm-receiving portion is located within the chamber of the heart, wherein the arms in the extended position point distally and form an acute angle with a longitudinal axis of the elongate housing, each arm configured to hold a suture portion a distance away from the outer diameter of the arm-receiving portion at or near a distal end of the arm; and a plurality of needles slidably received in the elongate housing proximal to the arm-receiving portion, each needle being associated with a needle lumen extending at least partially along the length of the elongate housing, each needle lumen having a needle guide at a distal end of the needle lumen, each needle guide having an angled surface extending away from the longitudinal axis of the elongate housing towards a needle aperture, each needle aperture being positioned proximal to the plurality of arms, wherein each needle is movable in a proximal-to-distal direction along the longitudinal axis of the elongate body along its respective needle lumen and outwardly through its respective needle aperture through heart tissue into engagement with the suture portion held by one of the arms when the plurality of arms are in their extended positions, the needles further being retractable away from the arms back through the heart tissue to draw the suture portions through the heart tissue, wherein the arms, needle lumens, needle guides and needle apertures are configured such that the needle guides are located within the transapical opening between the inner and outer surfaces of the heart when the arm-receiving portion is positioned within the chamber of the heart and such that the needles are moveable from within the transapical opening between the inner and outer surfaces of the heart through the heart tissue and penetrate through the inner surface of the heart radially outward of the transapical opening when the arms are extended inside the chamber of the heart.

In another embodiment, a method for closing a transapical opening in a wall of the heart, is provided. The method includes advancing a suturing device at least partially through the transapical opening, the suturing device including, an elongate body having a proximal end and a distal end and a handle at the proximal end of the elongate body configured to be manipulated from outside of the heart, a needle sheath positioned distal to the distal end of the elongate body, an arm sheath positioned distal to a distal end of the needle sheath, a tapered or rounded tip positioned distal to a distal end of the arm sheath and configured to be delivered through the transapical opening and into a ventricle of the heart, four arms proximal to the tip arranged symmetrically about an outer diameter of the arm sheath, each arm configured to hold a suture portion a distance away from the outer diameter of the arm sheath at or near a distal end of the arm, the arms being extendable from said arm sheath from a retracted position within the arm sheath to an extended position, wherein the arms in the extended position point distally and form an acute angle with a longitudinal axis of the elongate body, and four needles slidably housed in said elongate body, each needle being associated with a needle lumen extending at least partially along the length of the elongate body and at least partially along the length of the needle sheath, each needle lumen having a needle guide at a distal end of the needle lumen, each needle guide having an angled surface extending away from the longitudinal axis of the elongate body towards a needle aperture, each needle aperture being positioned proximal to the four arms, wherein each needle is movable in a proximal-to-distal direction along the longitudinal axis of the elongate body along its respective needle lumen and outwardly from the needle sheath through its respective needle aperture to pass through heart tissue into engagement with the suture portion held by one of the arms, the needles further being retractable away from the arms back through the heart tissue to draw the suture portions through the heart tissue. The method also includes positioning the suturing device such that the four arms are positioned within the ventricle of the heart and a distal end of each needle aperture is positioned within the transapical opening, extending the arms from the suturing device from the retracted position to the extended position in the ventricle of the heart, extending the needles from a position within the transapical opening through the wall of the heart in a proximal-to-distal direction along the longitudinal axis of the elongate body and outwardly from the elongate body into engagement with the suture portions held by the arms, retracting the needles through the wall of the heart to draw the suture portions through the wall of the heart, retracting the arms from the extended position to the retracted position, withdrawing the suturing device from the transapical opening, and closing the transapical opening with the suture portions.

In another embodiment, a suturing device for closing a transapical opening extending through a wall of the heart between inner and outer surfaces of the heart is provided. The suturing device includes an elongate housing having a proximal end and a distal end configured to be delivered through the transapical opening into a chamber of the heart, the elongate housing having a needle-receiving portion and an arm-receiving portion distal to the needle-receiving portion, a handle at the proximal end of the elongate housing configured to be manipulated from outside of the heart, a plurality of arms arranged about an outer diameter of the arm-receiving portion of the elongate housing, the arms being extendable from the arm-receiving portion from a retracted position within the arm-receiving portion to an extended position when the arm-receiving portion is located within the chamber of the heart, wherein the arms in the extended position point distally and form an acute angle with a longitudinal axis of the elongate housing, each arm configured to hold a suture portion a distance away from the outer diameter of the arm-receiving portion at or near a distal end of the arm, a plurality of needles slidably received in the needle-receiving portion of the elongate housing, the needle-receiving portion having a larger cross-sectional dimension than the arm-receiving portion and having a distal end proximal to the arm-receiving portion, each needle being associated with a needle lumen extending at least partially along the length of the elongate housing and at least partially along the length of the needle-receiving portion, each needle further being associated with a needle aperture at the distal end of the needle-receiving portion, wherein each needle is movable in a proximal-to-distal direction along the longitudinal axis of the elongate housing along its respective needle lumen and out of the distal end of the needle-receiving portion through its respective needle aperture to pass through heart tissue into engagement with the suture portion held by one of the arms when the plurality of arms are in their extended positions, each of the needles being slidable parallel to each other as they move in the proximal-to-distal direction, the needles further being retractable away from the arms back through the heart tissue to draw the suture portions through the heart tissue, wherein the arms, needle lumens, and needle apertures are configured such that the needle apertures are located outside of the heart and face the outer surface of the heart when the arm-receiving portion is positioned within the chamber of the heart and such that the needles are moveable from outside of the heart through the outer surface of the heart, through the heart tissue and penetrate through the inner surface of the heart radially outward of the transapical opening when the arms are extended inside the chamber of the heart.

In another embodiment, a method for closing a transapical opening in a wall of the heart is provided. The method includes, advancing a suturing device at least partially through the transapical opening, the suturing device including an elongate body having a proximal end and a distal end and a handle at the proximal end of the elongate body configured to be manipulated from outside of the heart, a needle sheath positioned distal to the distal end of the elongate body, an arm sheath positioned distal to a distal end of the needle sheath, the arm sheath having a diameter less than a diameter of the elongate body, a tip positioned distal to a distal end of the arm sheath and configured to be delivered through the transapical opening and into a ventricle of the heart, four arms proximal to the tip arranged symmetrically about an outer diameter of the arm sheath, each arm configured to hold a suture portion a distance away from the outer diameter of the arm sheath at or near a distal end of the arm, the arms being extendable from said arm sheath from a retracted position to an extended position, wherein the arms in the extended position point distally and form an acute angle with a longitudinal axis of the elongate body, and four needles slidably housed in said elongate body, each needle being associated with a needle lumen extending at least partially along the length of the elongate body and at least partially along the length of the needle sheath, each needle further being associated with a needle aperture at the distal end of the needle sheath, wherein each needle is movable in a proximal-to-distal direction along the longitudinal axis of the elongate body along its respective needle lumen and out of the distal end of the needle sheath through its respective needle aperture to pass through heart tissue into engagement with the suture portion held by one of the arms, each of the needles being slidable parallel to each other as they move in the proximal-to-distal direction, the needles further being retractable away from the arms back through the heart tissue to draw the suture portions through the heart tissue. The method also includes positioning the suturing device such that the four arms are positioned within the ventricle of the heart and a distal end of the needle sheath is exterior to the wall of the heart, extending the arms from the suturing device from the retracted position to the extended position in the ventricle of the heart, extending the needles through the wall of the heart in a proximal-to-distal direction along an axis parallel to the longitudinal axis of the elongate body into engagement with the suture portions held by the arms, retracting the needles through the wall of the heart to draw the suture portions through the wall of the heart, retracting the arms from the extended position to the retracted position, withdrawing the suturing device from the transapical opening, and closing the transapical opening with the suture portions.

BRIEF DESCRIPTION OF THE DRAWINGS

The above-mentioned and other features disclosed herein are described below with reference to the drawings of specific embodiments. The illustrated embodiments are intended for illustration, but not limitation. The drawings contain the following figures.

DETAILED DESCRIPTION

Embodiments of suturing systems and methods for suturing biological tissue are disclosed herein. The suturing apparatuses and their methods of use can be useful in a variety of procedures, such as treating (e.g., closing) wounds and naturally or surgically created apertures or passageways. In embodiments described herein, the suturing systems and methods are used to close an opening in the apex of the heart. In other examples, the suturing devices can be used to treat an anatomical valve, such as a heart valve, including heart valves that may be weakened or stretched, or have other structural defects, such as congenital defects, that cause them to close improperly. One or more suturing devices can be used to treat or repair valves, such as the tricuspid, pulmonary, mitral, and aortic valves, for example. In some suturing procedures, a suturing system including a suturing device disclosed herein can be used to perform procedures such as edge-to-edge repair (like an Alfieri technique), suturing of ventricular spaces, suturing of the chordae, suturing in other locations in the heart, and the like. The suturing system can be used to close or reduce a variety of other tissue openings, lumens, hollow organs or natural or surgically created passageways in the body. The suturing system can also include one or more pledgets. The suturing system can further include a knot-tying/forming device.

Figure 1:
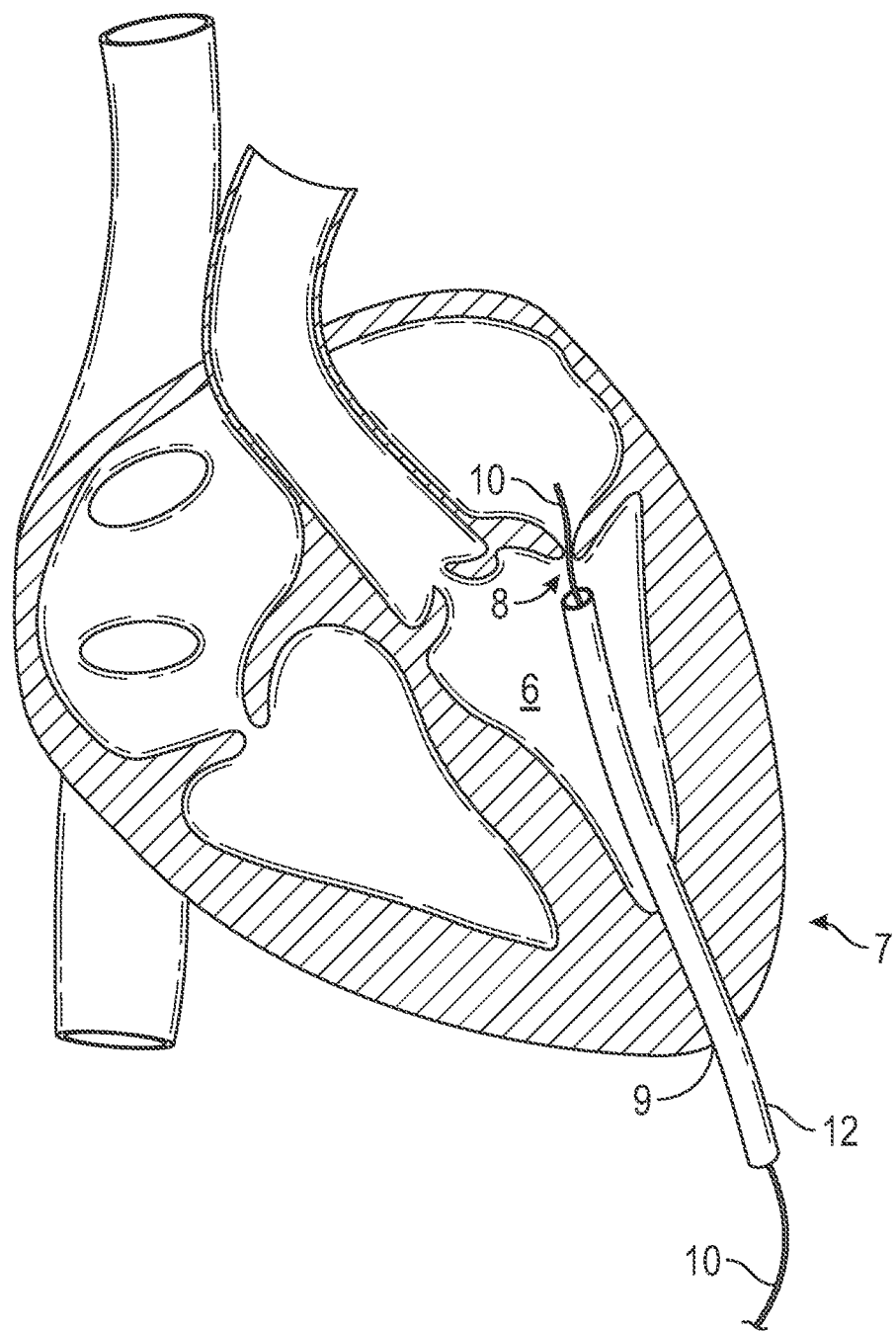
FIG. 1 depicts a schematic partial cross sectional view of an exemplifying treatment area, comprising a human heart.

FIG. 1 illustrates access through the apex 7 of the heart. As depicted in FIG. 1, a guidewire 10 is advanced into the left ventricle 6 of the heart through a puncture or opening 9 near an apex 7. The heart may be accessed through a limited thoracotomy, small trocar puncture, or small catheter puncture. With the guidewire 10 in place, the physician can insert a sheath 12 to the left ventricle 6. Treatment devices can be advanced through the lumen of the sheath 12. For example, treatment devices may be delivered to mitral valve 8 to repair or replace the valve. In an alternative embodiment, devices can be advanced over the guidewire 10 and positioned at or near a desired location without the need to insert an introducer sheath 12.

After the treatment of the heart is complete, a suitable suturing device, such as those disclosed herein, can be delivered through the apex to close the opening in the apex. In some embodiments, the introducer sheath 12 and/or guidewire 10 may be used to position the device within the opening 9. Alternatively, the suturing device may be directly inserted into the opening 9. FIGS. 2-13 illustrate one embodiment of a suturing device 100 that can be used to place suture through heart tissue to close the opening in the apex.

Figure 2:
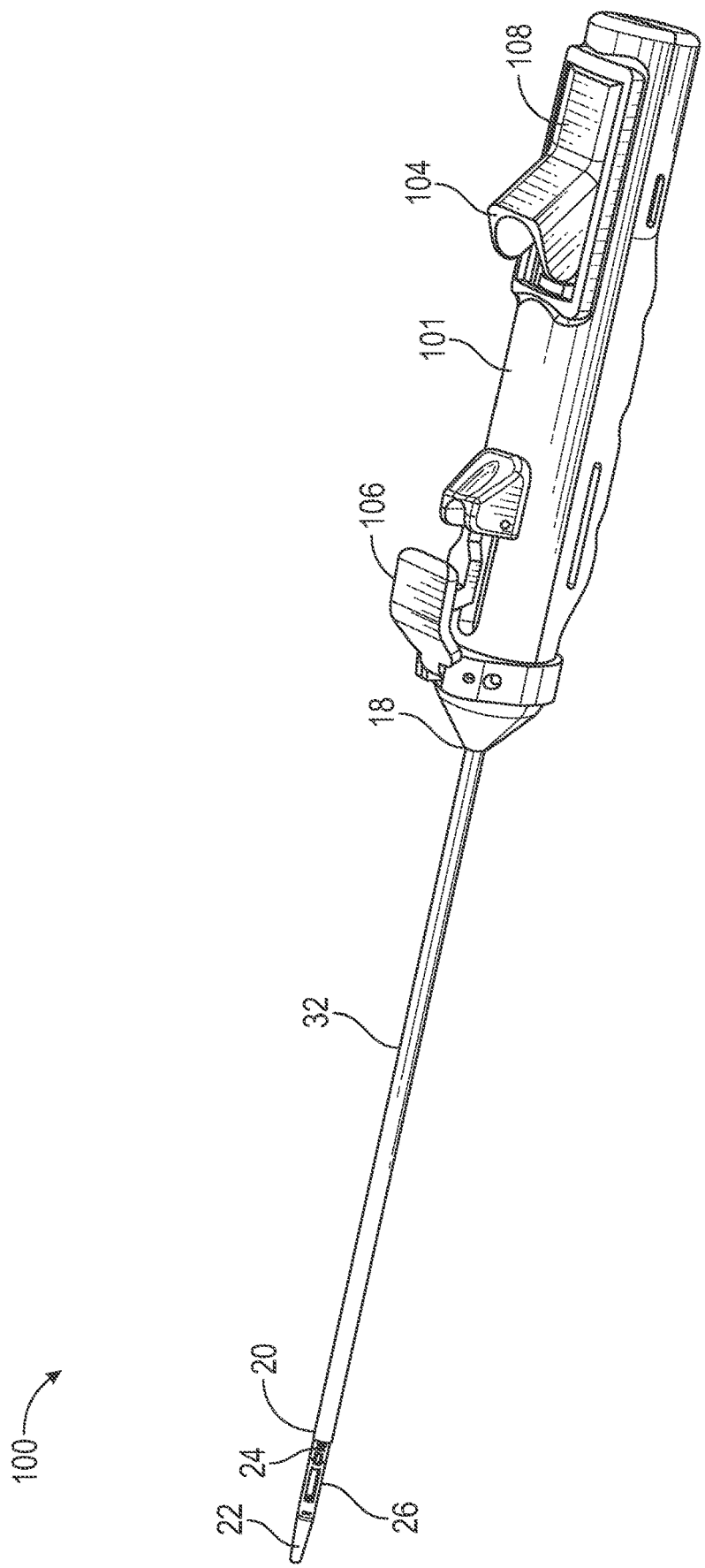
FIG. 2 depicts a perspective view of a suturing device 100 in a retracted configuration.

In the embodiment depicted in FIG. 2, the suturing device 100 includes an elongate body 32 having a proximal end 18 and a distal end 20, a handle portion 101, a needle sheath 24, an arm sheath 26, and a distal tip 22. In some embodiments, the needle sheath 24, arm sheath 26, and distal tip 22 can all form part of the elongate body 32 or be integral therewith. In some embodiments, the elongate body 32, needle sheath 24, arm sheath 26, and distal tip 22 can together form an elongate shaft or elongate housing that extends from the handle 101 to a distal end of the distal tip 22.

The handle portion 101 comprises actuators 104, 106, and 108. The handle portion 101 advantageously requires little manipulation during use. In some embodiments, the handle portion 101 can be operated with a single hand. The suturing apparatus can be used to close an opening located deep within the patient's tissue (e.g., the heart) without requiring the application of pressure over an extended period of time. As a result, the suturing apparatus can substantially reduce the recovery period following a medical procedure, thereby allowing the patient to return home more quickly and substantially reducing costs. The dimensions of the suturing device 100 can vary according to the approach to the transapical site and the particular medical procedure performed.

In some embodiments, the hollow elongate body 32 has a constant diameter of about 6-16 Fr and a length of about 15 to 80 cm, more preferably less than about 80 cm, 70 cm, 60 cm, 50 cm, 40 cm or 30 cm. In some embodiments, the elongate body 32 includes one or more selectively tapering portions along the longitudinal direction.

The needle sheath 24 extends distally from the distal end 20 of the elongate body 32. As described in further detail with respect to FIGS. 3 and 4, the needle sheath 24 can include one or more needle apertures from which a needle may extend and one or more needle guides shaped and sized to direct a needle in a particular direction. In some embodiments, the needle sheath 24 has a constant diameter of about 6-16 Fr. In some embodiments, the needle sheath 24 has the same diameter as the elongate body 32. In some embodiments, the needle sheath 24 is integrally formed with one or more of the elongate body 32, the arm sheath 26, and the distal tip 22, such that together they all comprise the elongate body.

The arm sheath 26 extends distally from the distal end of the needle sheath 24. As described in further detail with respect to FIGS. 3 and 4, the arm sheath 26 can include one or more arm apertures from which a suture arm can extend. In some embodiments, the arm sheath 24 has a constant diameter of about 6-16 Fr. In some embodiments, the arm sheath 26 has the same diameter as the elongate body 32. In some embodiments, the arm sheath 26 is integrally formed with one or more of the elongate body 32, the needle sheath 24, and the distal tip 22.

The distal tip 22 extends distally from the arm sheath 26. The distal tip 22 can taper distally to a smaller diameter. In some embodiments, the distal tip 22 is integrally formed with one or more of the elongate body 32, the needle sheath 24, and the arm sheath 26.

Figure 3:
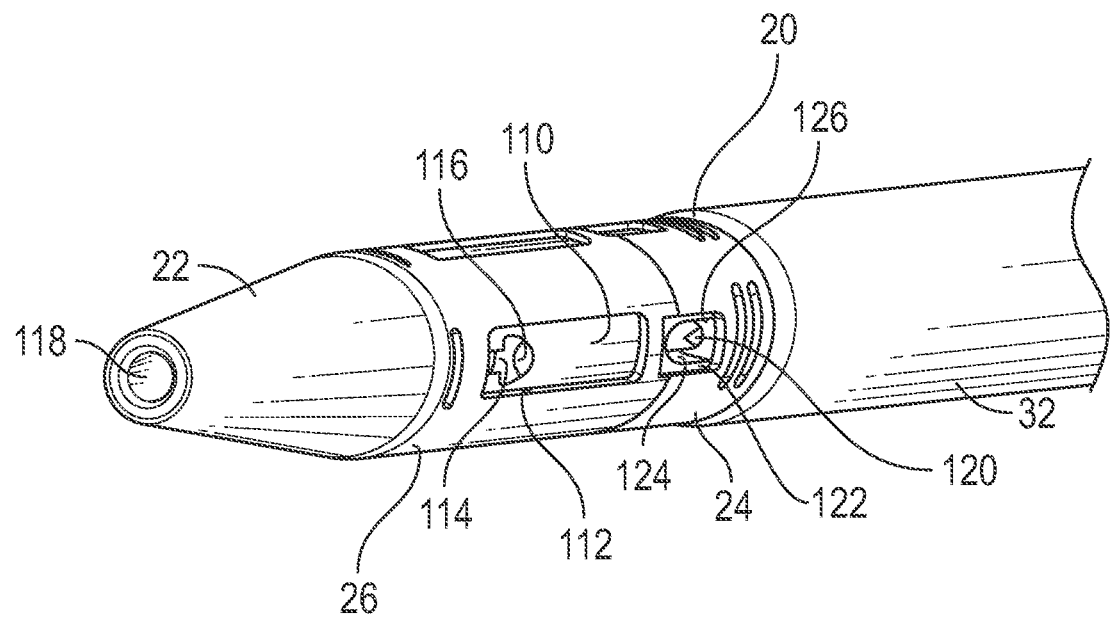
FIG. 3 depicts a perspective view of a distal portion of the suturing device 100 in the retracted configuration.
Figure 4:
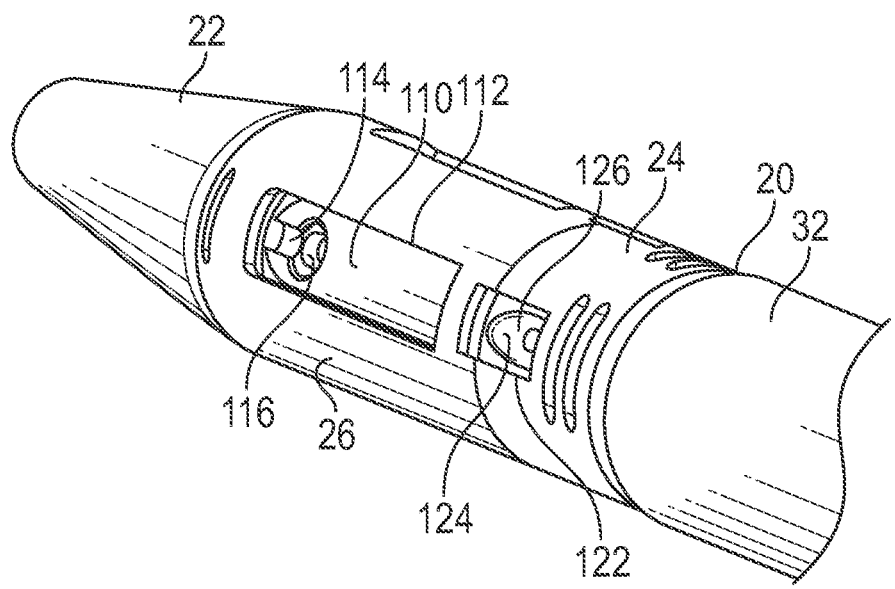
FIG. 4 depicts a perspective view of a distal portion of the suturing device 100 in the retracted configuration.

FIGS. 3-4 depict a distal end of the suturing device 100 in a retracted configuration. As shown in FIGS. 3 and 4, the arm sheath 26 can include one or more arm apertures 112 from which one or more suture arms 110 can extend. Each suture arm 110 can include a suture clasp 114 positioned near a distal end of the arm 110. The suture clasp 114 can hold an end or other portion of a suture. Each of the suture arms 110 can be pre-loaded with the ends of a suture before operation. The ends of the suture can pass from the suture clasps 114 through a distal hole 118 in the distal tip 22 whereby the ends of the suture enter the distal tip 22 and can be passed proximally through the hollow elongate body 32. In some embodiments, each end of the suture can include a capture portion having a loop that can be tied onto the ends of the suture clasp 114 or otherwise positioned within the suture clasp 114. For example, in some embodiments, each capture portion is positioned within an opening of the suture clasp 114. It is contemplated however that the capture portions are not restricted solely to tied loops, rather other types of capture portions can be utilized such as, by way of example, spheres or ferrules. Examples of suture capture portions are shown and described in U.S. Pat. No. 8,348,962 entitled "SUTURING DEVICE AND METHOD" and filed on Aug. 14, 2006, the entirety of which is hereby incorporated by reference.

Figure 5:
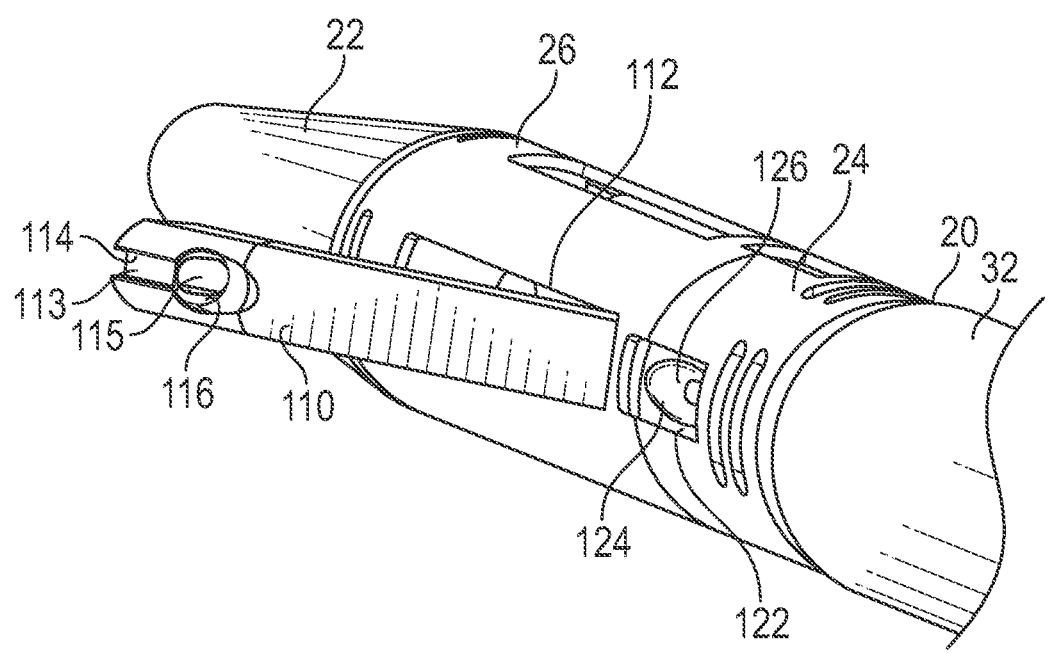
FIG. 5 depicts a perspective view of a distal portion of the suturing device 100 showing a suture arm 110 in an extended position.
Figure 6:
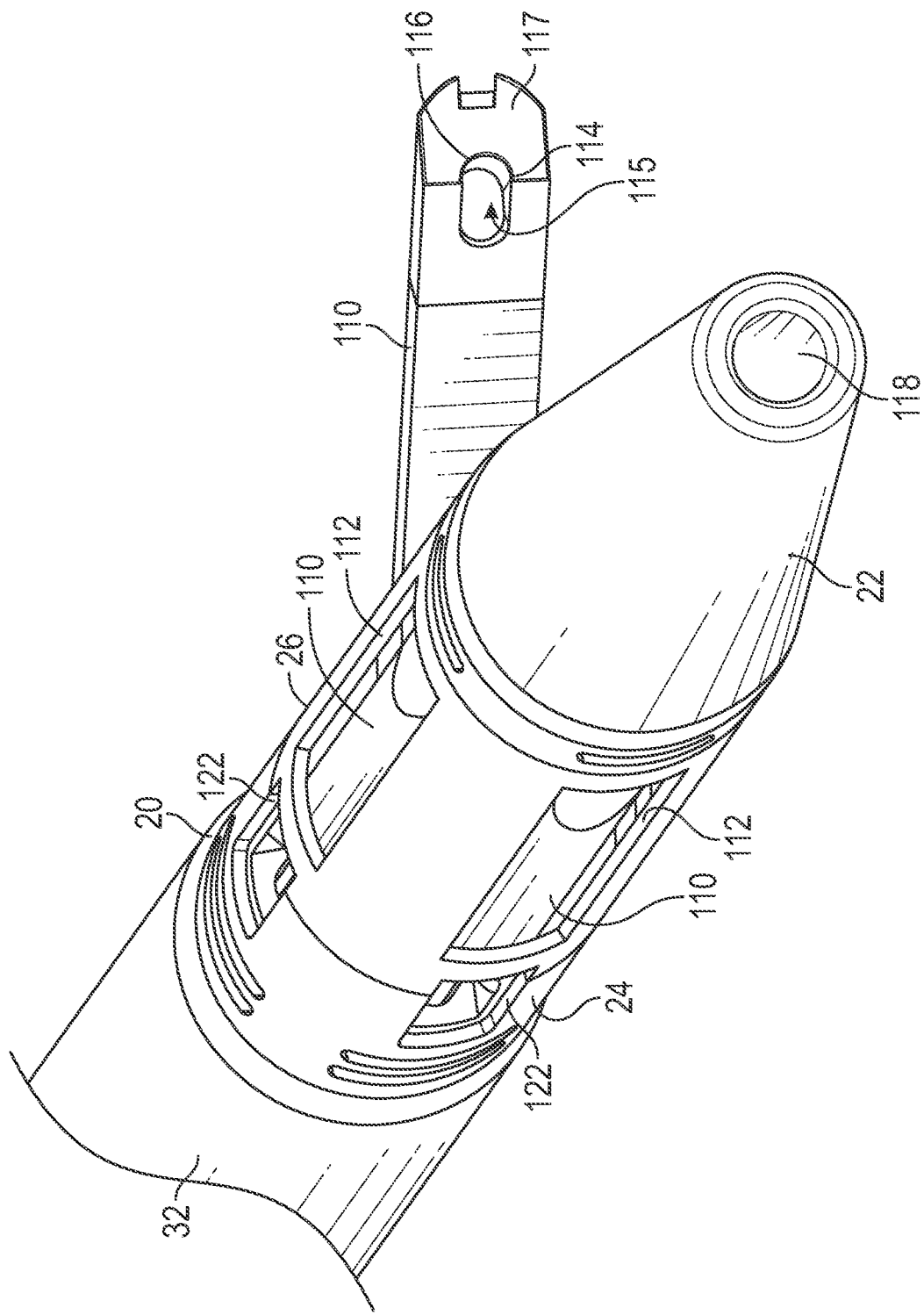
FIG. 6 depicts a perspective view of a distal portion of the suturing device 100 showing the suture arm 110 in an extended position.

As discussed in further detail with respect to FIGS. 5 and 6, the suture arms 110 can extend from the retracted position to an extended position in which the arms point distally and form an acute angle with a longitudinal axis of the elongate body 32.

The suturing device 100 of FIGS. 1-13 can include four arm apertures 112, each arm aperture corresponding to one of four suture arms 110. However, the suturing device 100 can include any number of arm apertures and any number of suture arms. For example, the arm sheath 26 can include one aperture, two apertures, three apertures, four apertures, five apertures, six apertures, or any other suitable number of apertures 112. In some embodiments, the suturing device 100 can include one suture arm, two suture arms, three suture arms, four suture arms, five suture arms, six suture arms, or any other suitable number of suture arms 110. In some embodiments, the suture arms 110 of the suturing device 100 can be arranged symmetrically about the outer diameter of the arm sheath 26.

As shown in FIGS. 3 and 4, the needle sheath 24 can include one or more needle apertures 122, and one or more needle guides 124. Each needle guide 124 can form part of a needle lumen 126 extending at least partially along the length of the elongate body 32. A plurality of needles 120 can be slidably housed within the elongate body 32. In the retracted configuration each needle 120 can reside within one of the needle lumens 126. As shown in FIGS. 3 and 4, a distal end of each needle 120 may extend into an interior section of the needle sheath 24 in the retracted configuration. As explained in further detail with respect to FIGS. 7 and 8A-8B, each needle 120 can move in a proximal-to-distal direction along the longitudinal axis of the elongate 32 body along its respective needle lumen 126.

Figure 7:
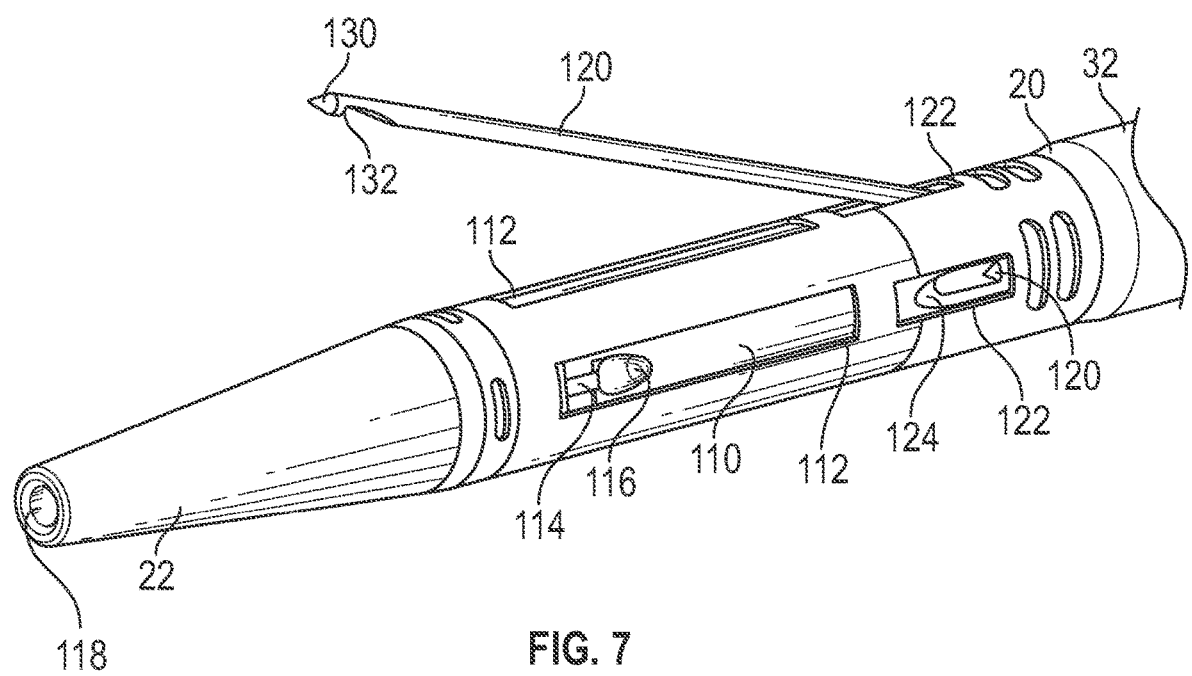
FIG. 7 depicts a perspective view of a distal portion of the suturing device 100 showing the needle 120 in an extended position.
Figure 8A:
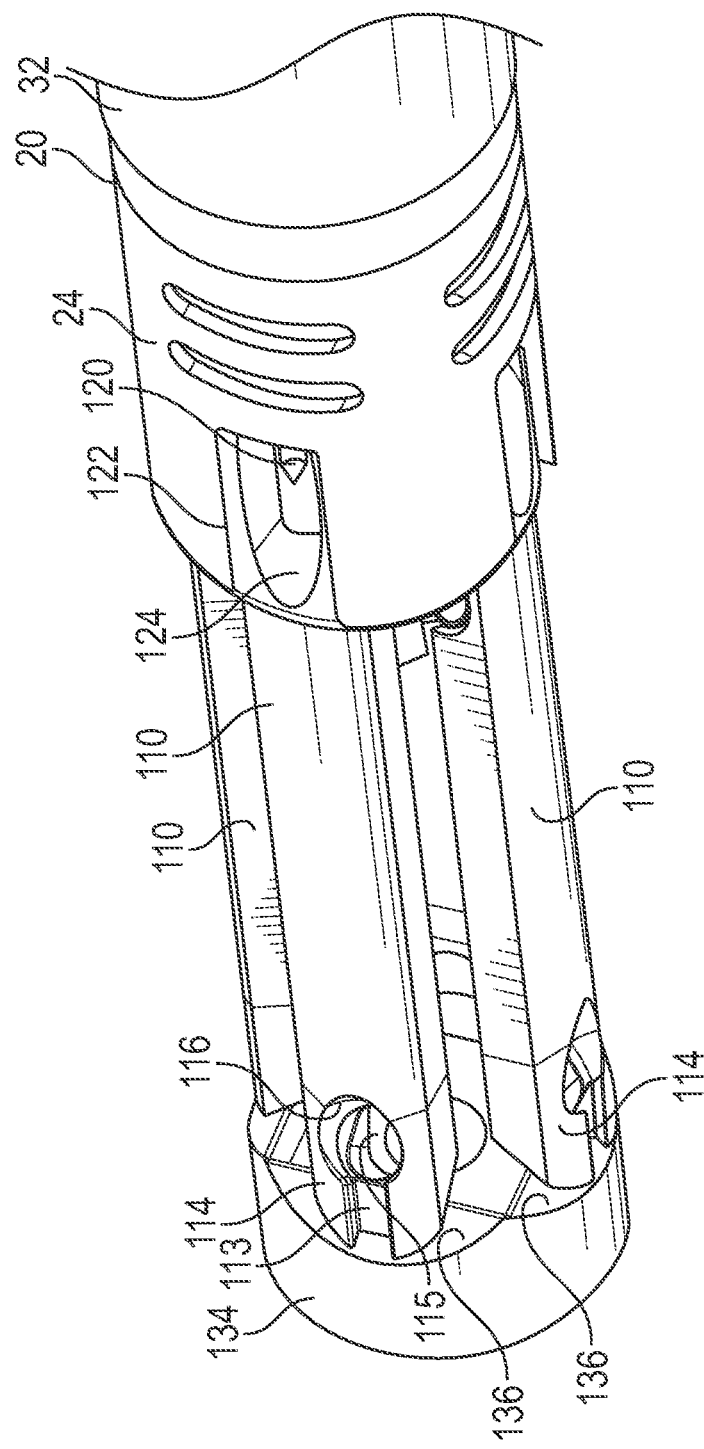
FIG. 8A depicts a perspective view of a distal portion of the suturing device 100 with the arm sheath 26 removed.
Figure 8B:
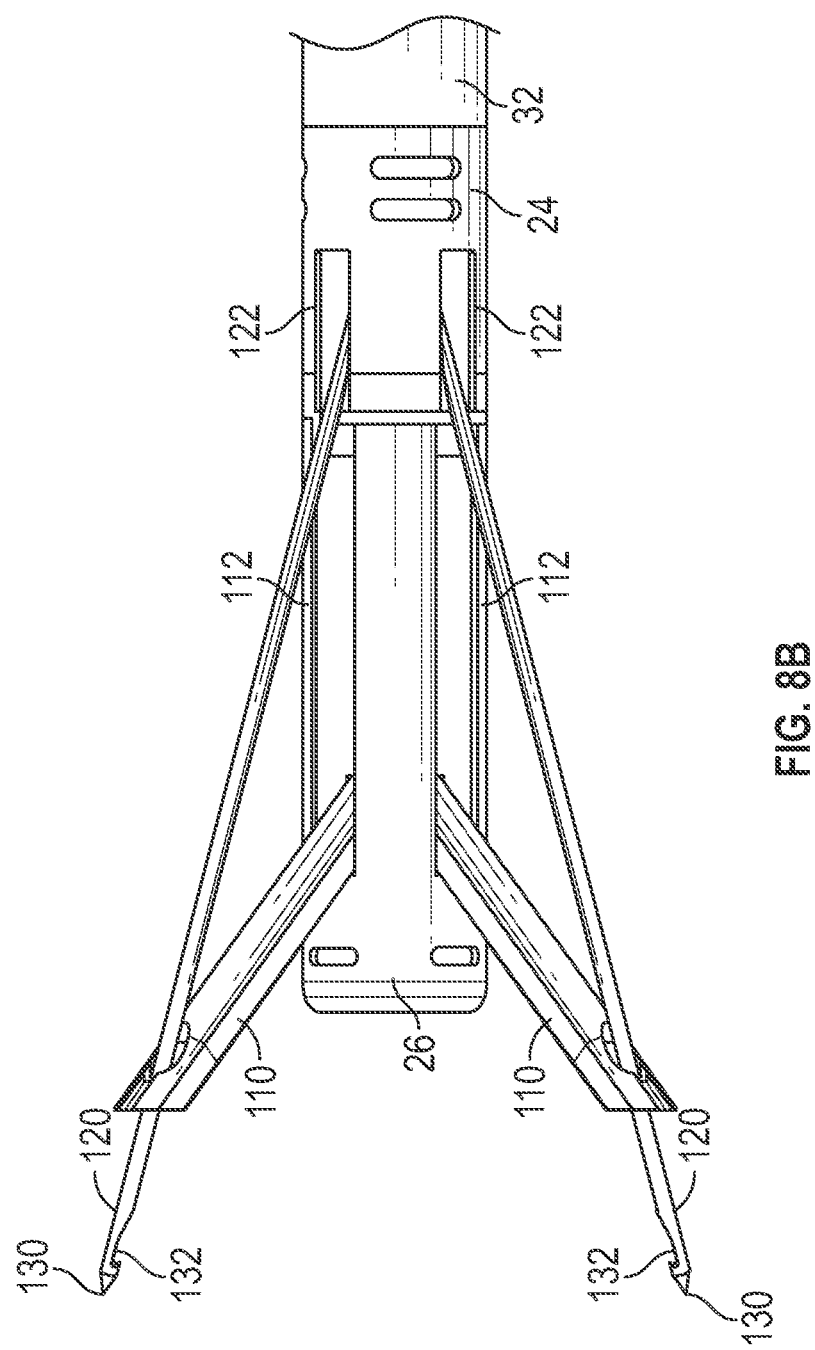
FIG. 8B depicts a side view of a distal portion of the suturing device 100 showing the arms 110 and needles 120 in an extended position.

Each needle guide 124 can include a curved or angled surface, angling away from the longitudinal axis of the elongate body 32. As a needle 120 moves distally along its needle lumen 126, the needle guide 124 can direct the needle 120 out of its respective needle aperture 122 at an angle relative to the longitudinal axis of the elongate body 32 to an extended configuration, as illustrated in FIGS. 7 and 8A-8B. When the needles 120 are in an extended position, each needle 120 can engage a suture portion held by one of the suture arms 110.

The needles 120 can be flexible and made of a material with shape memory, such as SUPERFLEX NITINOL™. Alternatively, the needles 120 can be comprised of spring steel, surgical stainless steel or any variation thereof. Each of the needles 120 can have a diameter of about 0.019 inches, but needles with other diameters can be used in accordance with the particular medical procedure contemplated. In some embodiments, each needle 120 includes a proximal section having a first diameter and a distal section having a second diameter smaller than the first diameter. The diameter of the proximal section of the needle 120 can be of a sufficient thickness to penetrate the tissue of the heart without deflection. The diameter of the distal section can be of sufficient size to clasp a suture portion held by one of the arms 110. Use of a needle 120 with two different diameters can allow for the diameter at the distal end of the needle 120 to be relatively smaller than the diameter of a needle 120 having only a single diameter throughout while still penetrating the tissue of the heart. Such a needle 120 can allow for smaller arms 110 and clasps 114.

When the suture arms 110 are retracted into the arm apertures 112 and the needles 120 are retracted into the needle apertures 122, the arms 110 and the needles 120 are recessed within the suturing device, as shown in FIGS. 3 and 4. This prevents the arms 110 and the needles 120 from causing tissue damage while the distal end portion passes through a biological structure.

The suturing device 100 of FIGS. 1-13 includes four needles 120. However, the suturing device 100 can include any number of needle apertures and any number of needles. For example, the suturing device can include one needle, two needles, three needles, four needles, five needles, six needles, or any other suitable number of needles 120.

FIGS. 5 and 6 depict the distal end of the suturing device 100 with one of the suture arms 110 in an extended position. As described in further detail herein with respect to FIGS. 9 and 10, each suture arm 110 can be deployed from the retracted configuration to the extended configuration by actuation of the actuator 104. The actuator 104 is configured to cause the suture arms 110 to move in a proximal-to-distal direction along a longitudinal axis of the elongate body 32 such that a proximal end of each arm 110 moves from a proximal end of its respective arm aperture 112 to a distal end of the arm aperture 112. As each suture arm 110 translates in a proximal-to-distal direction, a distal end of each suture arm 110 can contact a ramp positioned within the arm sheath 26, as discussed further with respect to FIGS. 8A and 8B. The ramp can be curved or angled to cause the arm 110 to extend at an acute angle with respect to the longitudinal axis of the elongate body 32.

As shown in FIGS. 5 and 6, each suture clasp 114 can include a track 113, an opening 115, a tapered or beveled portion 116, and a distal surface 117. The capture portion of the suture can be positioned within the opening 115 through which one of the needles 120 can extend to grasp the capture portion. A length of the suture can extend along the track 113, which can facilitate alignment of the capture portion, and into the elongate body 32. The beveled or tapered section 116 extends about the opening 116 and is configured to receive a needle when the suture arms 110 extend through the suture apertures 112. The taper can help guide the needles into the suture clasps and toward a suture portion within a clasp. This can be beneficial if a needle has prolapsed slightly or otherwise deviated from a preferred alignment, such as an alignment with the center of a suture clasp opening 116. The distal surface 117 is angled with respect to a longitudinal axis of the arm 110 to conform to the angle of the ramps positioned within the arm sheath 26 so that the suture arms 110 do not extend beyond the circumference of the arm sheath 26 when in the retracted position. In some embodiments, the distal surface 117 is positioned at a 45° angle with respect to the longitudinal axis of the arm 110.

FIG. 7 depicts the distal end of the suturing device 100 with one of the needles 120 in an extended position. Each needle 120 extends from its respective needle aperture 122 at an angle to the longitudinal axis of the elongate body 32 due to the angled surface of its respective needle guide 124. As described in further detail herein with respect to FIGS. 9 and 10, each needle 120 can be deployed from the retracted configuration to the extended configuration shown in FIG. 7 by actuation of the actuator 106. The actuator 106 can be further manipulated to retract the needle 120 back into the needle sheath 24.

FIG. 8A depicts the distal end of the suturing device 100 with the arm sheath 26 removed. As shown in FIG. 8A, a spreading member 134 is positioned within the distal end of the arm sheath 26. The spreading member includes a plurality of ramps 136. Each ramp 136 provides an angled or curved surface configured to cause one of the arms 110 to extend at an acute angle to the longitudinal axis of the elongate body 32 when the arm 110 comes into contact with the ramp 136 when moving in the proximal-to-distal direction. In some embodiments, the arms 110 may extend at a 45° angle with respect to the longitudinal axis of the elongate body 32. In some embodiments, each ramp may be positioned at a 45° with respect to a longitudinal axis of the elongate body 32. When fully extended, a proximal end of each arm 110 can contact one of the ramps 136. In some embodiments, the angled surface of each ramp 136 can abut a proximal portion of the arm 110 to prevent the arm 110 from moving towards the longitudinal axis of the elongate body 32 when the arm 110 is in the extended portion.

FIG. 8B depicts the distal end of the suturing device 100 with the suture arms 110 and the needles 120 in an extended position. In comparison to FIG. 8A, the arms 110 are positioned at the distal end of the arm sheath 26 such that a proximal portion of each arms 110 abuts one of the ramps 136. As shown in FIGS. 7 and 8B, each needle 120 can include a tip 130 and a suture catch portion or hook 132. The tip 130 may be tapered or otherwise shaped to pass through the tissue of the heart. Each suture catch portion or hook 132 can be configured to engage a suture portion positioned within the suture clasp 114 of the suture arm 110 when the needle 120 extends through the suture clasp 114 of the suture arm 110. Once the hook 132 of the needle 120 has engaged the suture portion, the distal end of the needle 120 and the suture portion can be pulled proximally through the elongate body 32 which will cause the bent portion of the needle to be retracted along needle guide 124 into its respective needle lumen 126.

Figure 9:
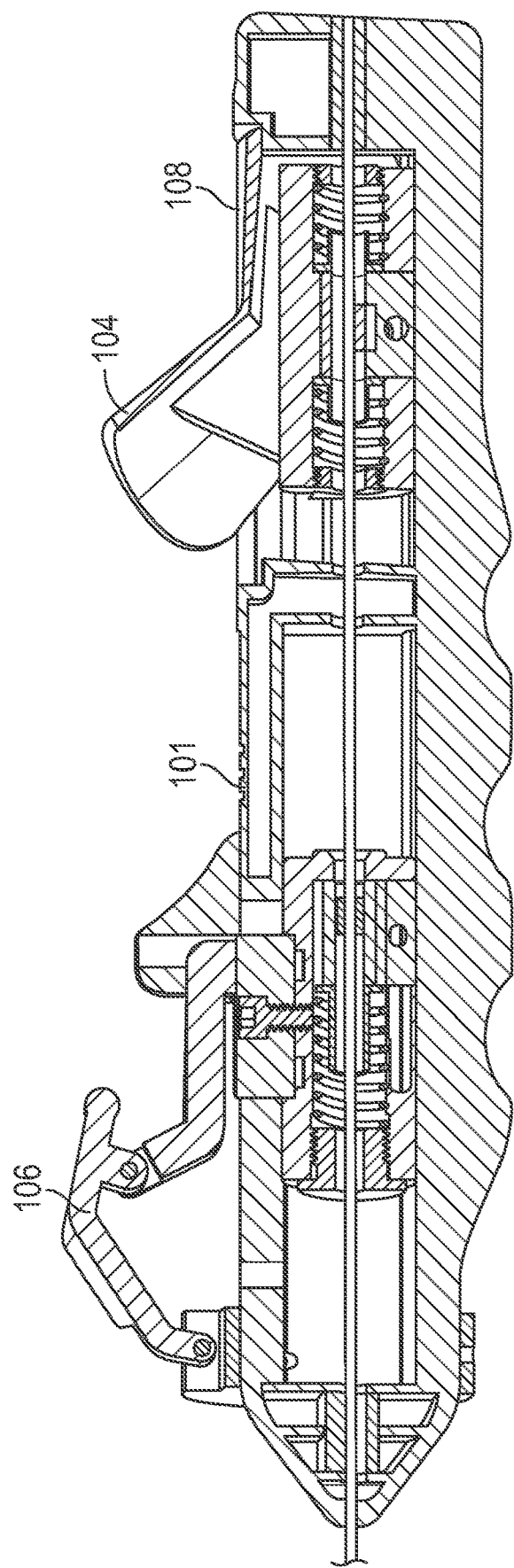
FIG. 9 depicts a cross-sectional view of a handle 101.
Figure 10:
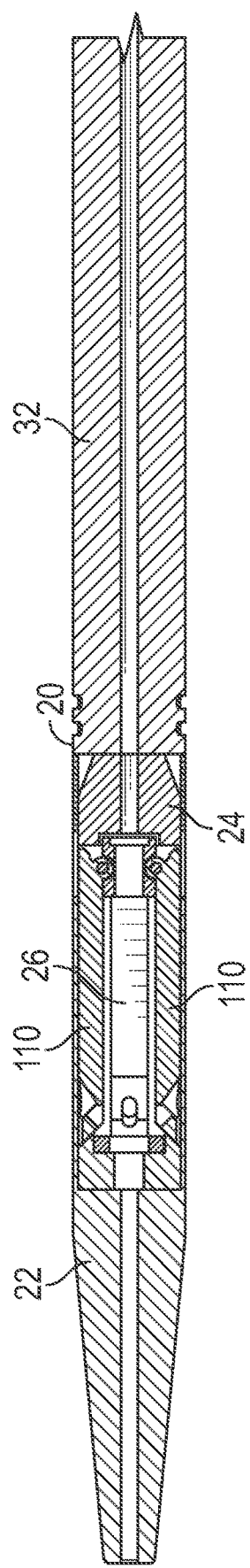
FIG. 10 depicts a cross-section view of a distal portion of the suturing device 100.

FIG. 9 depicts a cross-sectional view of the handle 101 showing the internal components thereof. FIG. 10 depicts a cross-sectional view of the distal end of the suturing device 101 showing the internal components of the elongate body 32, the needle sheath 24, the arm sheath 26 and the distal tip 22. As described herein, the actuator 104 can be actuated to cause one or more of the arms 110 to deploy from the retracted position to the extended position. In some embodiments, actuator 104 can be actuated to deploy each arm 110 at the same time. In some embodiments, individual arms 110 can be actuated. Actuator 106 can be actuated to deploy one or more of the needles 120 from the retracted position to the extended position. In some embodiments, actuator 106 can be actuated to deploy each needle 120 at the same time. In some embodiments, individual needles 120 can be actuated. The actuator 106 can further be manipulated to cause retraction of one or more of the needles 120. The actuator 108 can be actuated to retract one or more of the arms 110 from the extended position to the retracted position. In some embodiments, actuator 108 can be actuated to retract each arm 110 at the same time. In some embodiments, individual arms 110 can be retracted.

Figure 11:
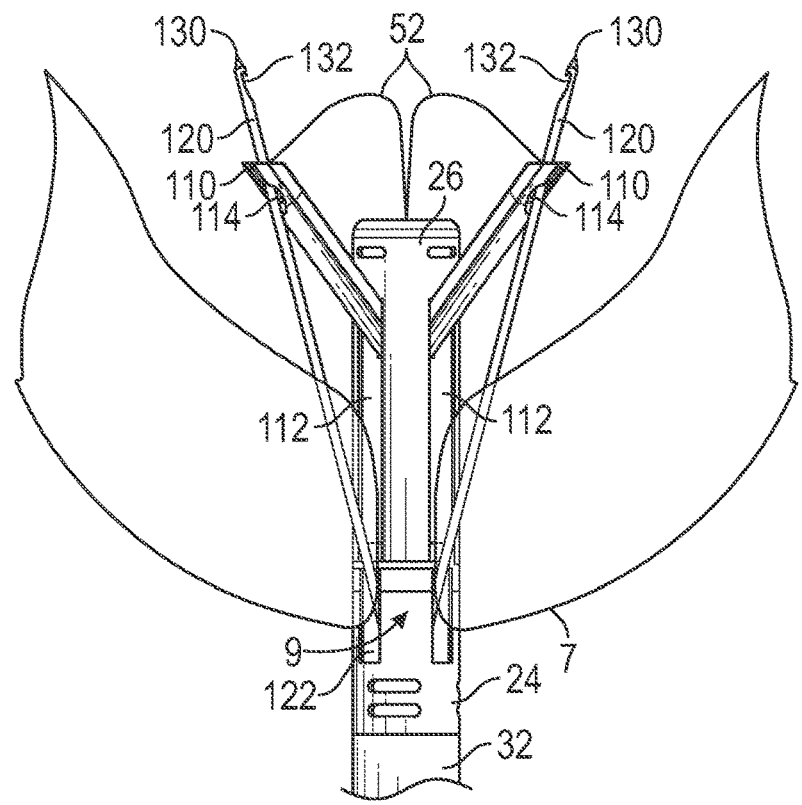
FIG. 11 depicts a method of placing a suture through a heart wall using the suturing device 100.
Figure 12:
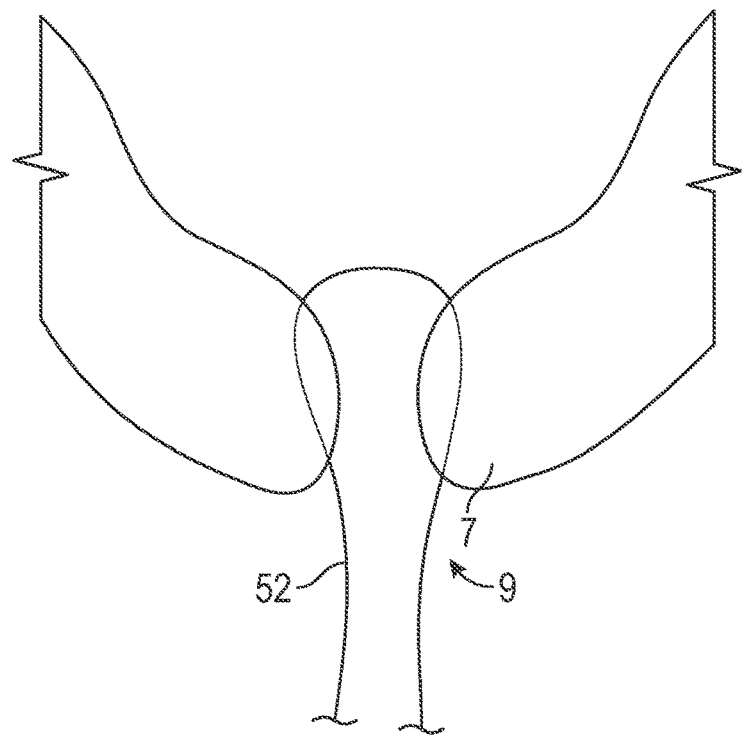
FIG. 12 depicts a suture 52 extending through the tissue adjacent a transapical opening.
Figure 13:
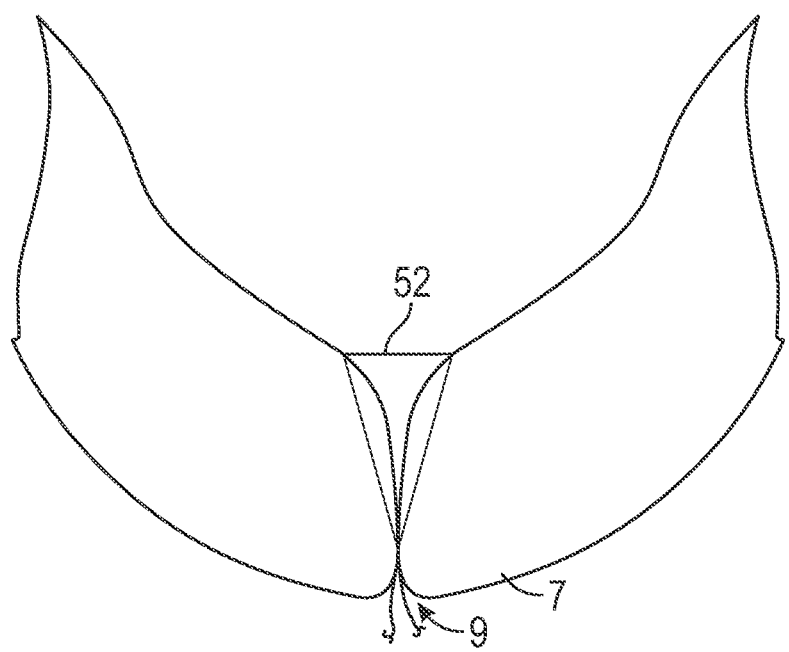
FIG. 13 depicts the suture 52 closing a transapical opening.

FIGS. 11-13 illustrate an embodiment of a method of closing a transapical opening using the suturing device 100 shown in FIGS. 1-10. The suturing device 100 can be introduced through the opening 9 near the apex 7. As indicated above, the suturing device 100 can be introduced into the opening with or without the aid of a guidewire 10 that may pass through a lumen of the elongate body 32 and the distal tip 22. The suturing device 100 can be positioned through the opening a sufficient distance to permit the arms 110 to be deployed within the ventricle 6 of the heart without damage to the surrounding tissue. The arms 110 can then be deployed within the ventricle 6.

With the arms 110 deployed, the device 100 can be retracted to cause the arms 110 to engage the heart internal wall tissue surrounding the opening 9. In some embodiments, the angle of each suture arm 110 may match an incline of the heart internal wall tissue surrounding the opening 9. The needle apertures 122 can be spaced apart from the arm apertures 112 such that the distal end of each needle aperture 122 is positioned within the transapical opening 9 when the arms 110 engage the heart internal wall tissue surrounding the opening 9. If the distal end of each needle aperture 122 is not positioned within the transapical opening 9 when the arms 110 engage the heart internal wall tissue, the suturing device 100 can be further positioned so that the distal end of each needle aperture 122 is positioned within the transapical opening 9.

After the needle apertures 122 are positioned within the transapical opening 9, the needles 120 can be advanced from a position within the transapical opening 9 through the heart wall tissue and into the ventricle 6 in a proximal-to-distal direction along the longitudinal axis of the elongate body 32 and outwardly from the needle sheath 24. FIG. 11 shows the needles 120 extended through the heart wall tissue from within the opening 9 and to the suture clasps 114 or beyond the suture clasps 114. The tip 22 is not shown in FIG. 11. After extending to or beyond the suture clasps 114, the needles 120 can be snatch the end portions of a suture 52 from the arms 110. For example, the needles 120 can be retracted to snatch the end portions of the suture 52.

The suture can be withdrawn through the heart tissue as the needles 120 are retracted into the elongate body 32. The arms 110 can then be retracted and the entire suturing device 100 can be withdrawn. The suture can be removed from the device and pulled through the heart tissue to result in the configuration as shown in FIG. 12, where the suture extends across the transapical opening along an inner surface of the left ventricle and exits the heart from within the transapical opening. Placing the suture along the inner surface of the left ventricle advantageously provides closure to the transapical opening from within the left ventricle. In this embodiment, with the suture exiting the heart from within the transapical opening rather than from the outer surface of the heart, tension applied on the suture can more easily draw the tissue surrounding the opening closed.

After the suture 52 has been placed, the suture ends can be tied together or a knot can be placed to close the opening 9, as shown in FIG. 13. In some embodiments, the placed suture 52 may be an initial suture that is used to then guide an additional suture through the sutured tissue. In such embodiments, the initial suture is removed from the patient and the additional suture is used to draw the opening closed.

Figure 24:
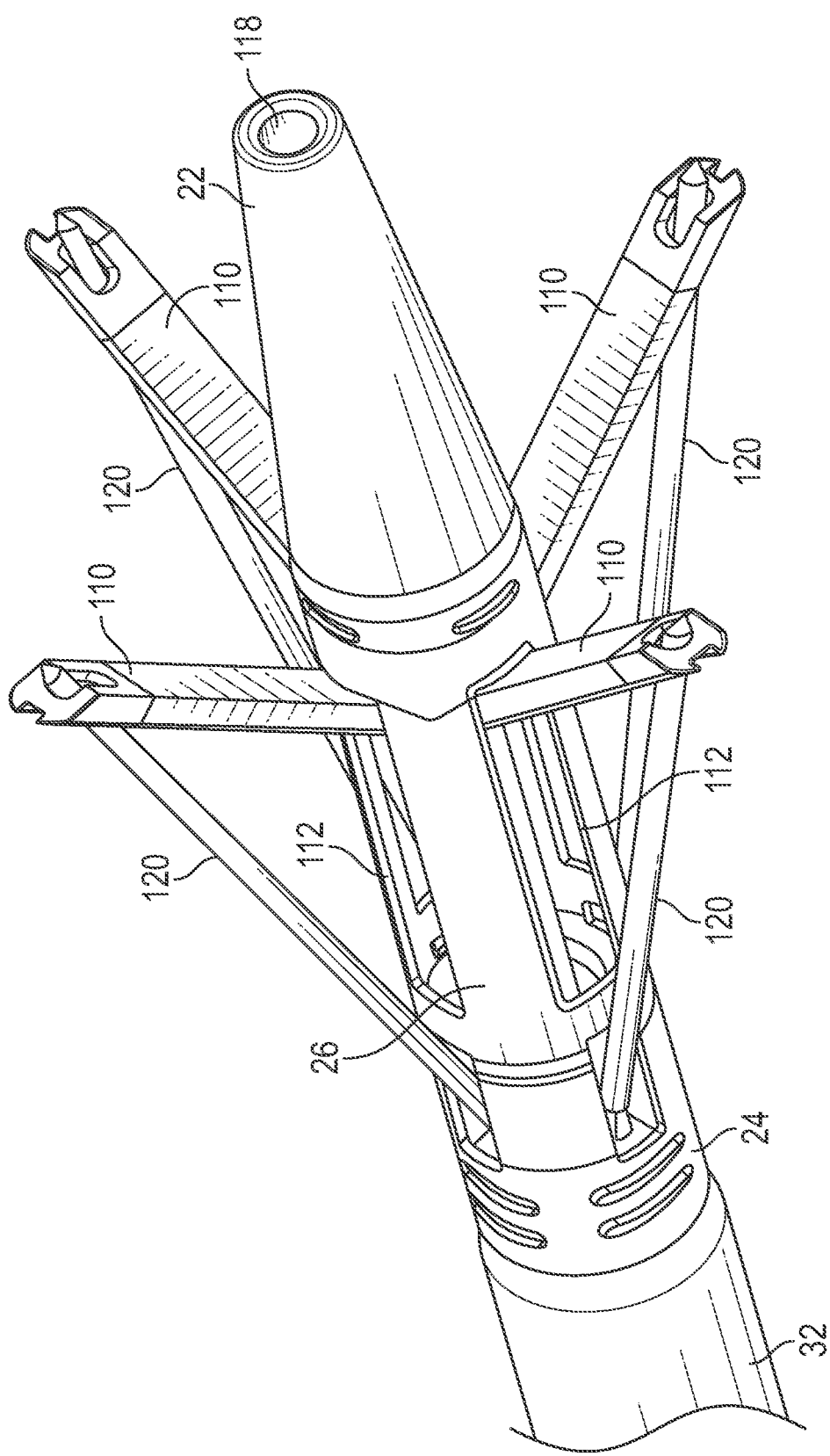
FIG. 24 depicts a perspective view of a distal end of the suture device 100 showing four suture arms 110 and four needles 120 in an extended position.

In some embodiments, the two suture arms 110 shown in FIG. 11 hold opposite ends of the suture 52. Although only two needles 120 and two arms 110 are shown in the extended position in FIG. 11, one of skill in the art would understand that two additional arms 110 can be deployed to hold the ends of a second suture, which can be grasped by two additional needles 120. The first pair of suture arms 110 holding opposite ends of the first suture can be diametrically opposed to one another. The second pair of suture arms 110 holding the ends of the second suture can also be diametrically opposed to one another. The four suture arms 110 forming the first pair and second pair of suture arms 110 can be arranged symmetrically about the outer diameter of the arm sheath 26. In some embodiments, the first suture 52 may cross over or under the second suture when extended across the transapical opening 9. An example of an embodiment having four suture arms 110 and four needles 120 in an extended configuration is shown in FIG. 24. Examples of the use of multiple sutures to close a transapical opening are described in U.S. patent application Ser. No. 13/016,897 entitled "METHODS AND APPARATUSES FOR SUTURING OF CARDIAC OPENINGS" and filed on Jan. 28, 2011, the entirety of which is hereby incorporated by reference. The embodiments described herein are improvements over those described in U.S. patent application Ser. No. 13/016,897, but one of skill in the art would understand that some of the features described in U.S. patent application Ser. No. 13/016,897 can be used in the embodiments described herein.

Although the device 100 can be used for suturing transapical openings of the heart, the suturing device 100 can be used to suture other tissues such as, by way of example, a patent ductus arteriosus, a patent foramen ovale (PFO), a heart defect, a puncture wound, and the like.

FIGS. 14-23 illustrate an embodiment of a suturing device 300 that can be used to place suture through heart tissue to close the opening in the apex. The suturing device 300 can include many of the same or similar features to the suturing device 100 described herein.

Figure 14:
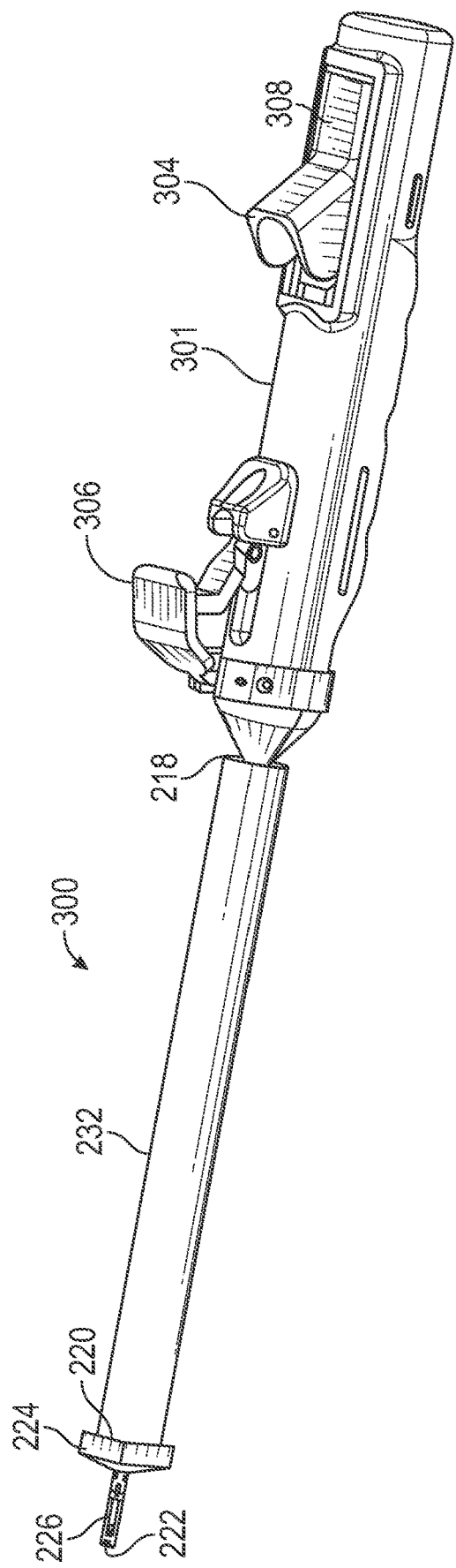
FIG. 14 depicts a perspective view of a suturing device 300 in a retracted configuration.

In the embodiment depicted in FIG. 14, the suturing device 300 includes an elongate body 232 having a proximal end 218 and a distal end 220, a handle portion 301, a needle sheath 224, an arm sheath 226, and a distal tip 222. In some embodiments, the needle sheath 224, arm sheath 226, and distal tip 222 can all form part of the elongate body 232 or be integral therewith. In some embodiments, the elongate body 232, needle sheath 224, arm sheath 226, and distal tip 222 can together form an elongate shaft or elongate housing that extends from the handle 301 to a distal end of the distal tip 222.

The handle portion 301 comprises actuators 304, 306, and 308. The handle portion 301 advantageously requires little manipulation during use. In some embodiments, the handle portion 301 can be operated with a single hand. The suturing apparatus can be used to close an opening located deep within the patient's tissue (e.g., the heart) without requiring the application of pressure over an extended period of time. As a result, the suturing apparatus can substantially reduce the recovery period following a medical procedure, thereby allowing the patient to return home more quickly and substantially reducing costs. The dimensions of the suturing device 300 can vary according to the approach to the transapical site and the particular medical procedure performed.

In some embodiments, the hollow elongate body 232 has a constant diameter of about 6-16 Fr and a length of about 15 to 80 cm, more preferably less than about 80 cm, 70 cm, 60 cm, 50 cm, 40 cm or 30 cm. In some embodiments, the elongate body 232 includes one or more selectively tapering portions along the longitudinal direction.

The needle sheath 224 extends distally from the distal end 220 of the elongate body 232. As described in further detail with respect to FIGS. 15 and 16, the needle sheath 224 can include one or more needle apertures from which a needle may extend. As shown in FIG. 14, the needle sheath 224 has a cross-section that is generally square or rectangular in shape and has a width extending beyond the diameter of the elongate body 32. However, the needle sheath 224 can have any suitable shape. In some embodiments, the needle sheath 224 can have a cylindrical cross-section. In some embodiments, the needle sheath 224 can have a constant diameter of about 6-16 Fr. In some embodiments, the needle sheath 224 has the same diameter as the elongate body 232. In some embodiments, the needle sheath 224 is integrally formed with one or more of the elongate body 232, the arm sheath 226, and the distal tip 222.

The arm sheath 226 extends distally from the distal end of the needle sheath 224. As described in further detail with respect to FIGS. 15 and 16, the arm sheath 226 can include one or more arm apertures from which a suture arm can extend. In some embodiments, the arm sheath 224 has a constant diameter of about 6-16 Fr. In some embodiments, the arm sheath 226 has the same diameter as the elongate body 232. In some embodiments, the arm sheath 226 is integrally formed with one or more of the elongate body 232, the needle sheath 224, and the distal tip 222.

The distal tip 222 extends distally from the arm sheath 226. As shown in FIG. 14, the distal tip 222 can have a generally cylindrical cross-section. In some embodiments, the distal tip 222 has a constant diameter of about 6-16 Fr. In some embodiments, the distal tip 222 can taper distally to a smaller diameter. In some embodiments, the distal tip 222 is integrally formed with one or more of the elongate body 232, the needle sheath 224, and the arm sheath 226.

Figure 15:
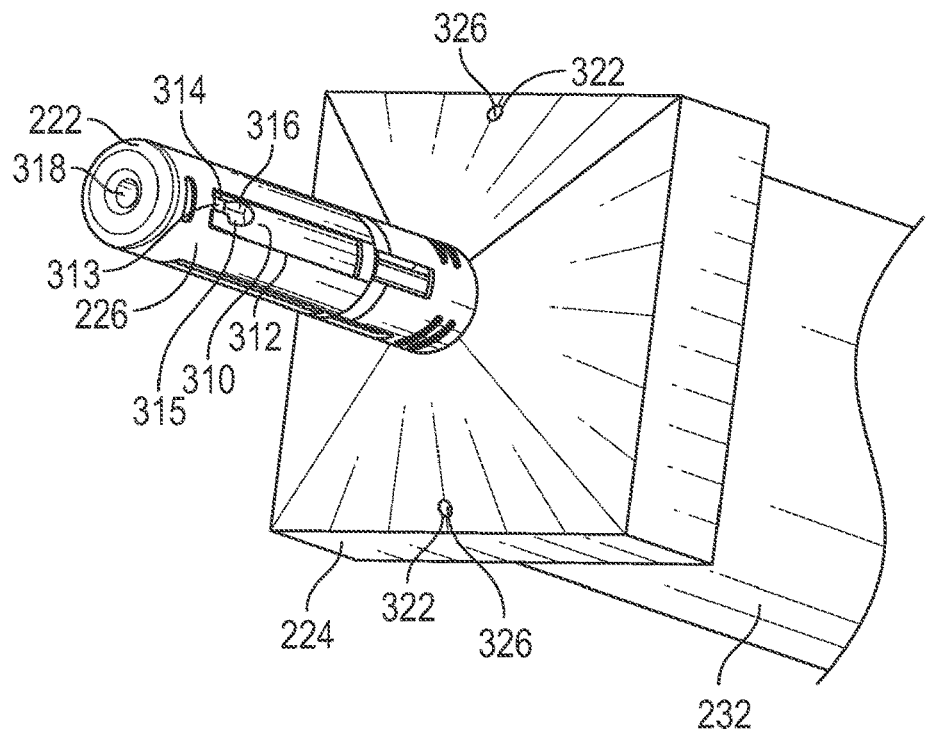
FIG. 15 depicts a perspective view of a distal portion of the suturing device 300 in the retracted configuration.
Figure 16:
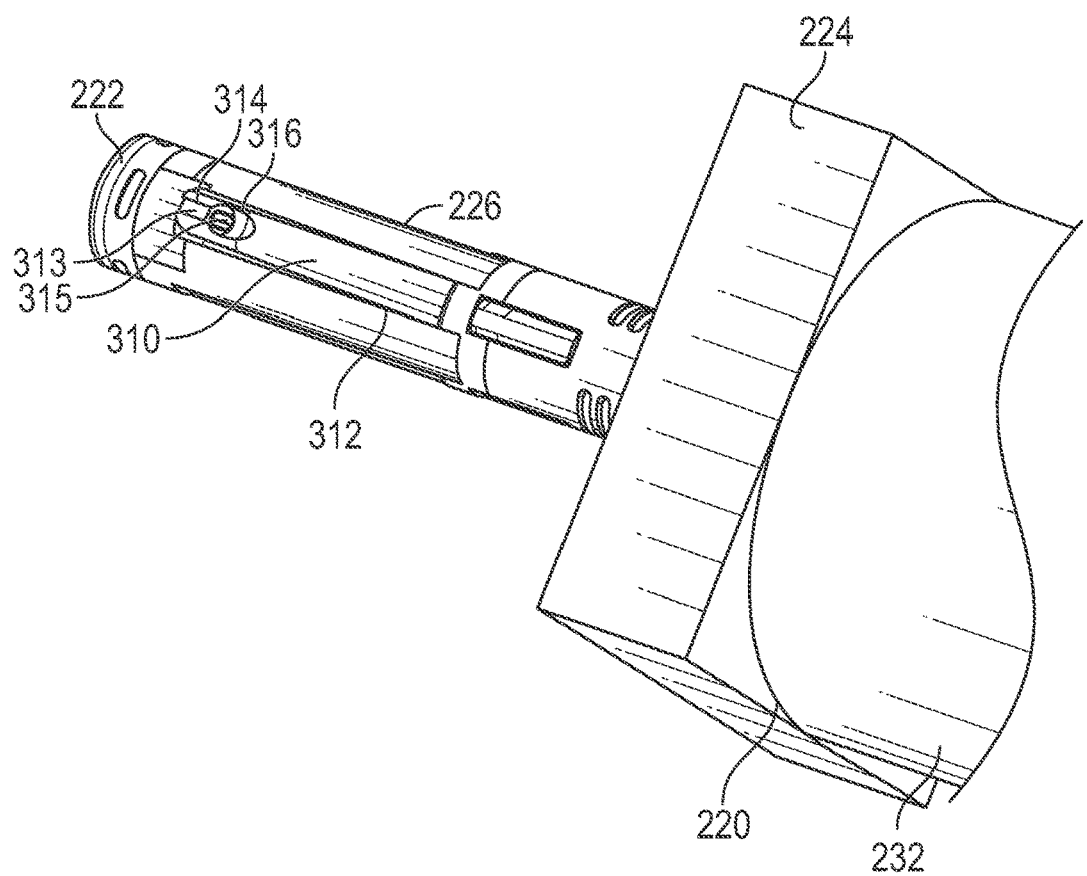
FIG. 16 depicts a perspective view of a distal portion of the suturing device 300 in the retracted configuration.

FIGS. 15 and 16 depict the distal end of the suturing device 100 in a retracted configuration. As shown in FIGS. 15 and 16, the arm sheath 226 can include one or more arm apertures 312 from which one or more suture arms 310 can extend. Each suture arm 310 can include a suture clasp 314 positioned near a distal end of the arm 314. The suture clasp 314 can hold an end or other portion of a suture. Each of the suture arms 310 can be pre-loaded with the ends of a suture before operation. The ends of the suture can pass from the suture clasps 314 through a distal hole 318 in the distal tip 222 whereby the ends of the suture enter the distal end 220 and can be passed proximally through the hollow elongate body 232. In some embodiments, each end of the suture can include a capture portion having a loop that can be tied onto the ends of the suture clasps 314 or otherwise positioned within the suture clasp 314. For example, in some embodiments, each capture portion is positioned within an opening of the suture clasp 314. It is contemplated however that the capture portions are not restricted solely to tied loops, rather other types of capture portions can be utilized such as, by way of example, spheres or ferrules.

Figure 22:
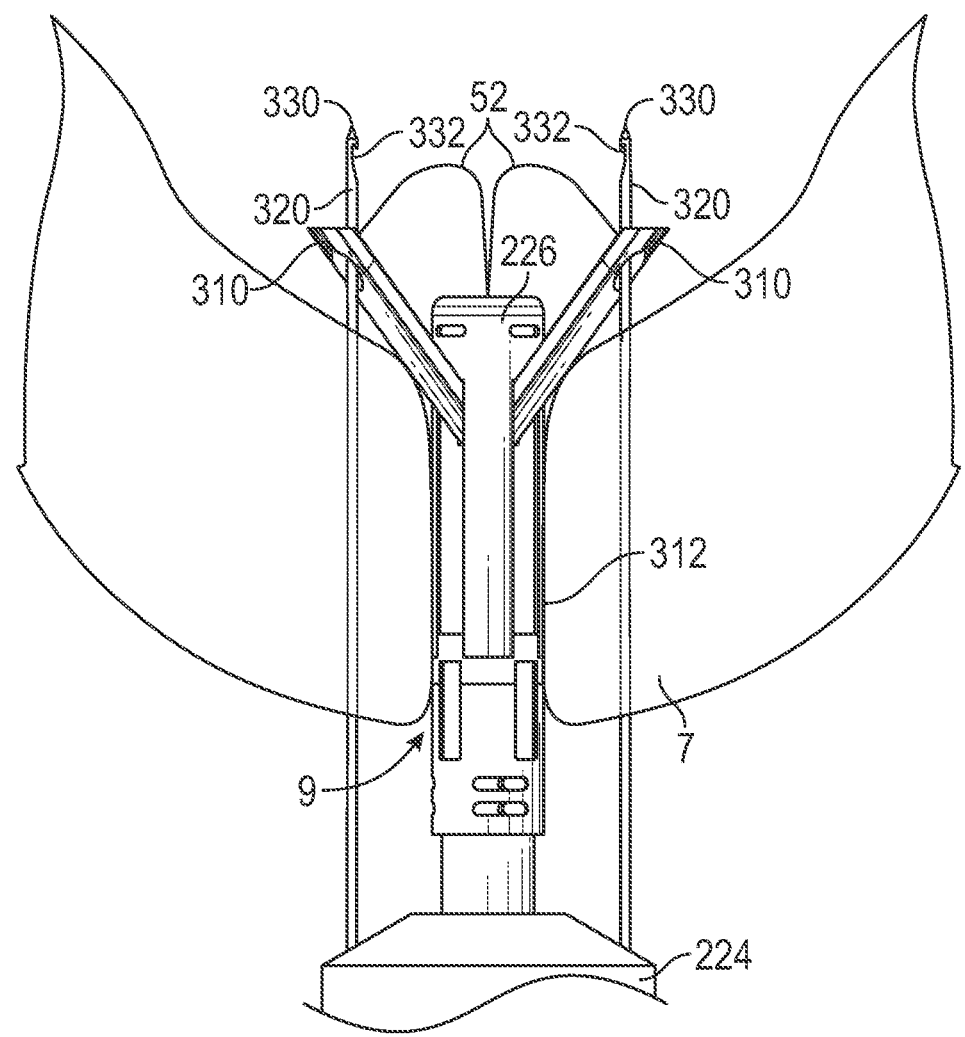
FIG. 22 depicts a method of placing a suture through a heart wall using the suturing device 300.

As discussed in further detail with respect to FIGS. 22 and 23, the suture arms 310 can extend from the retracted position to an extended position in which the arms point distally and form an acute angle with a longitudinal axis of the elongate body 332.

The suturing device 300 of FIGS. 14-23 includes four arm apertures 312, each corresponding to one of four suture arms 310. However, the suturing device 300 can include any number of arm apertures and any number of suture arms. For example, the arm sheath 226 can include one aperture, two apertures, three apertures, four apertures, five apertures, six apertures, or any other suitable number of apertures 312. In some embodiments, the suturing device 300 can include one suture arm, two suture arms, three suture arms, four suture arms, five suture arms, six suture arms, or any other suitable number of suture arms 310. In some embodiments, the suture arms 310 of the suturing device 300 can be arranged symmetrically about the outer diameter of the needle sheath 312.

As shown in FIGS. 15 and 16, the needle sheath 224 can include one or more needle apertures 322. Each aperture 322 can be positioned at a distal end of a needle lumen 326 extending at least partially along the length of the elongate body 232. Each needle lumen 326 can extend parallel to the longitudinal axis of the elongate body 232. A plurality of needles can be slidably housed within the elongate body 232. In the retracted configuration each needle can reside within one of the needle lumens 326. As explained in further detail with respect to FIG. 19, each needle can move in a proximal-to-distal direction along the longitudinal axis of the elongate 332 body along its respective needle lumen 320.

When the needles are in an extended position, each needle 120 can engage a suture portion held by one of the suture arms 310. The needles can be flexible and made of a material with shape memory, such as SUPERFLEX NITINOL™. Alternatively, the needles can be comprised of spring steel, surgical stainless steel or any variation thereof. In some embodiments, the needles can be made of a rigid material configured to prevent or reduce bending of the needle. Each of the needles can have a diameter of about 0.019 inches, but needles with other diameters can be used in accordance with the particular medical procedure contemplated. In some embodiments, each needle includes a proximal section having a first diameter and a distal section having a second diameter smaller than the first diameter. The diameter of the proximal section of the needle can be of a sufficient thickness to penetrate the tissue of the heart without deflection. The diameter of the distal section can be of sufficient size to clasp a suture portion held by one of the arms 310. Use of a needle with two different diameters can allow for the diameter at the distal end of the needle to be relatively smaller than the diameter of a needle having only a single diameter throughout while still penetrating the tissue of the heart. Such a needle can allow for smaller arms 310 and clasps 314.

When the suture arms 310 are retracted into the arm apertures 312 and the needles are retracted into the needle apertures 322, the arms 310 and the needles are recessed within the suturing device, as shown in FIGS. 15 and 16. This prevents the arms 310 and the needles from causing tissue damage while the distal end portion passes through a biological structure.

The suturing device 300 of FIGS. 14-23 includes four needles 320. Only two needle apertures are shown in in FIG. 15, but one of skill in the art would understand that there can be a needle aperture 322 for each needle 320 of the suturing device 300. The suturing device 300 can include any number of needle apertures and any number of needles. For example, the suturing device can include one needle, two needles, three needles, four needles, five needles, six needles, or any other suitable number of needles.

Figure 17:
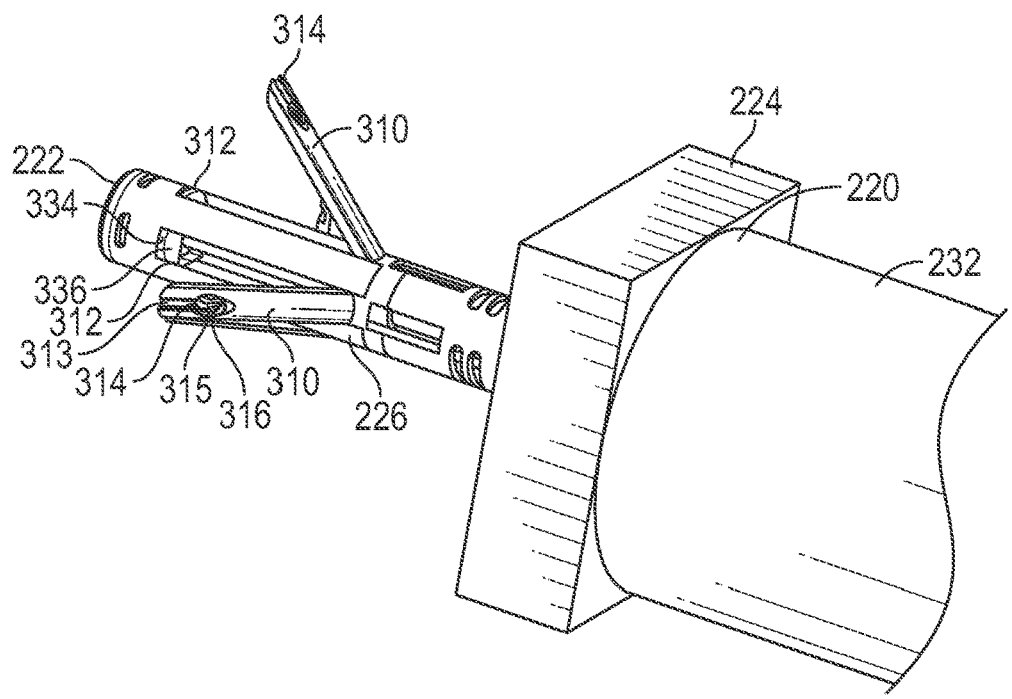
FIG. 17 depicts a perspective view of a distal portion of the suturing device 300 showing suture arms 310 in an extended position.
Figure 18:
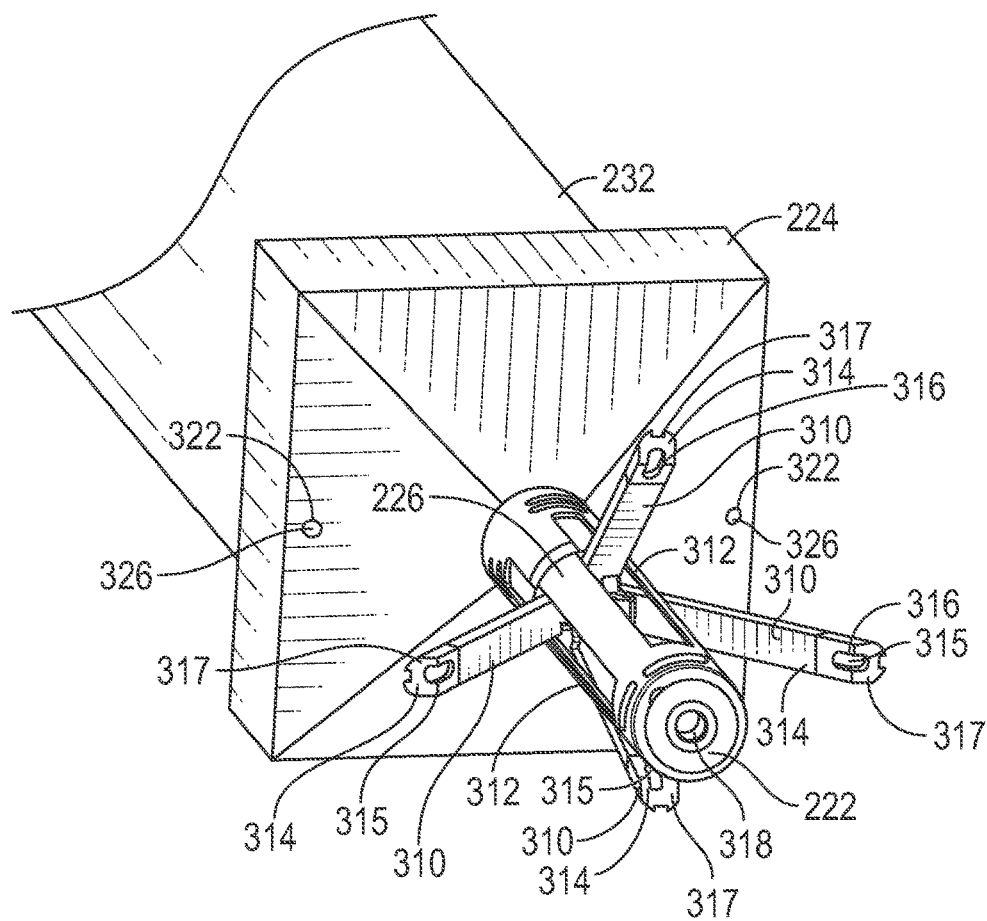
FIG. 18 depicts a perspective view of a distal portion of the suturing device 300 showing suture arms 310 in an extended position.

FIGS. 17 and 18 depict the distal end of the suturing device 300 with the suture arms 310 in an extended position. As described in further detail herein with respect to FIGS. 20 and 21, each suture arm 310 can be deployed from the retracted configuration to the extended configuration by actuation of the actuator 304. The actuator 304 is configured to cause the suture arms 310 to move in a proximal-to-distal direction along a longitudinal axis of the elongate body 232 such that a proximal end of each arm 310 moves from a proximal end of its respective arm aperture 312 to a distal end of the arm aperture 312. As shown in FIG. 17, a spreading member 334 is positioned within the distal end of the arm sheath 226. The spreading member 334 includes a plurality of ramps 336. Each ramp 336 provides an angled or curved surface configured to cause one of the arms 310 to extend at an acute angle to the longitudinal axis of the elongate body 232 when the arm 310 comes into contact with the ramp 336 when moving in the proximal-to-distal direction. In some embodiments, the arms 310 may extend at a 450 angle with respect to the longitudinal axis of the elongate body 232. In some embodiments, each ramp may be positioned at a 45° with respect to a longitudinal axis of the elongate body 232. When fully extended, a proximal end of each arm 310 can contact one of the ramps 336. In some embodiments, the angled surface of each ramp 336 can abut a proximal portion of the arm 310 to prevent the arm 310 from moving towards the longitudinal axis of the elongate body 232 when the arm 310 is in the extended portion.

As shown in FIGS. 17 and 18, each suture clasp 314 can include a track 313, an opening 315, a tapered or beveled portion 316, and a distal surface 317. The capture portion of the suture can be positioned within the opening 315 through which one of the needles 320 can extend to grasp the capture portion. A length of the suture can extend along the track 313, which can facilitate alignment of the capture portion, and into the elongate body 232. The beveled or tapered section 316 extends about the opening 316 and is configured to receive a needle when the suture arms 310 extend through the suture apertures 312. The taper can help guide the needles into the suture clasps and toward a suture portion within a clasp. This can be beneficial if a needle has prolapsed slightly or otherwise deviated from a preferred alignment, such as an alignment with the center of a suture clasp opening 316. The distal surface 317 is angled with respect to a longitudinal axis of the arm 310 to conform to the angle of the ramps 336 positioned within the arm sheath 226 so that the suture arms 310 do not extend beyond the circumference of the arm sheath 226 when in the retracted position. In some embodiments, the distal surface 317 is positioned at a 45° angle with respect to the longitudinal axis of the arm 310.

Figure 19:
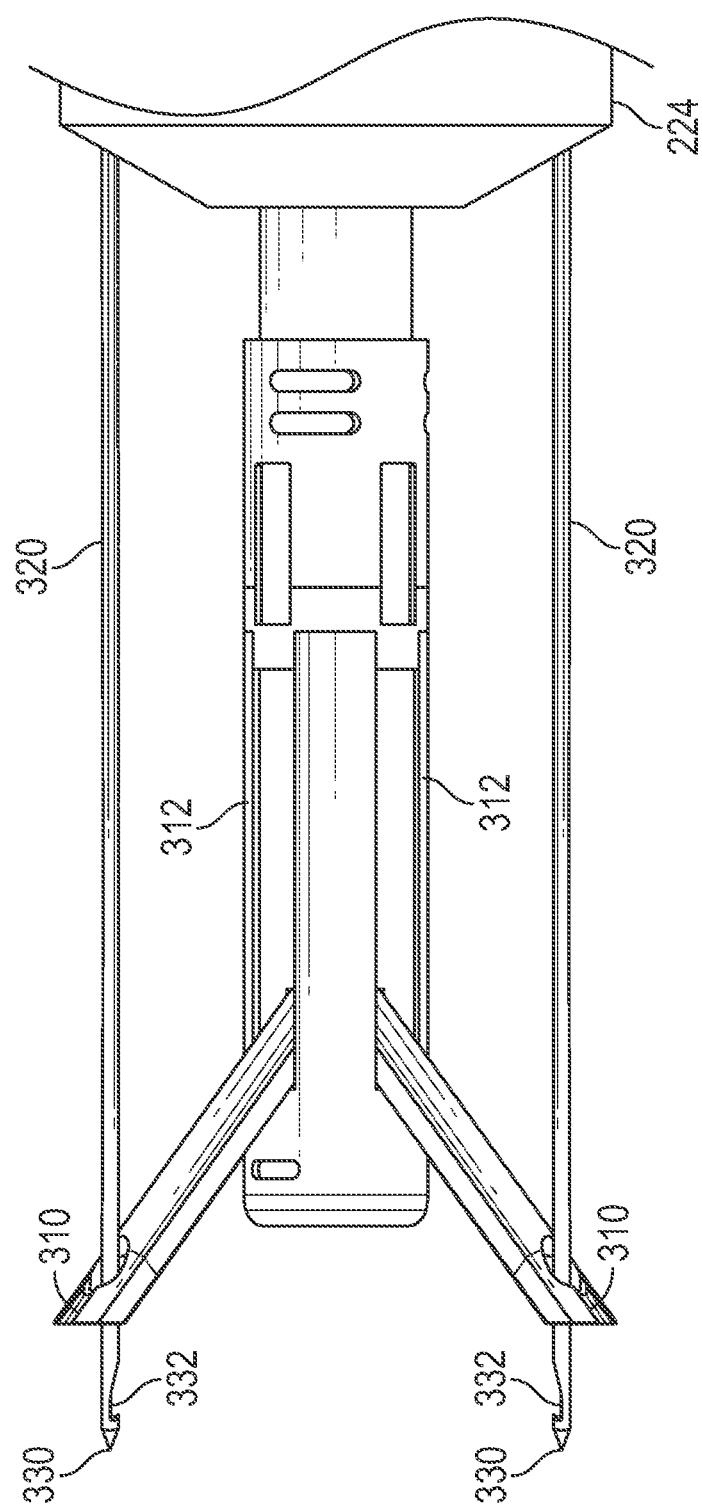
FIG. 19 depicts a perspective view of a distal portion of the suturing device 300 showing arms 310 and needles 320 in an extended position.

FIG. 19 depicts the distal end of the suturing device 300 with a plurality of needles 320 and suture arms 310 in an extended position. In comparison to FIGS. 17 and 18, the arms 310 are positioned at the distal end of the arm sheath 226 such that a proximal portion of each arms 310 abuts one of the ramps 336. Each needle 320 extends from its respective needle aperture 322 parallel to the longitudinal axis of the elongate body 232. As described in further detail herein with respect to FIGS. 20 and 21, each needle 320 can be deployed from the retracted configuration to the extended configuration shown in FIG. 19 by actuation of the actuator 306. The actuator 106 can be further manipulated to retract the needle 320 back into the needle sheath 224.

As shown in FIG. 19, each needle 320 can include a tip 330 and a suture catch portion or hook 332. The tip 330 may be tapered or otherwise shaped to pass through the tissue of the heart. Each suture catch portion or hook 332 can be configured to engage a suture portion positioned within the suture clasp 314 of the suture arm 310 when the needle 320 extends through the suture clasp 314 of the suture arm 310. Once the hook 332 of the needle 320 has engaged the suture portion, the distal end of the needle 320 and the suture portion can be pulled proximally through the elongate body 232 which will cause the needle to be retracted along its respective needle lumen 326.

Figure 20:
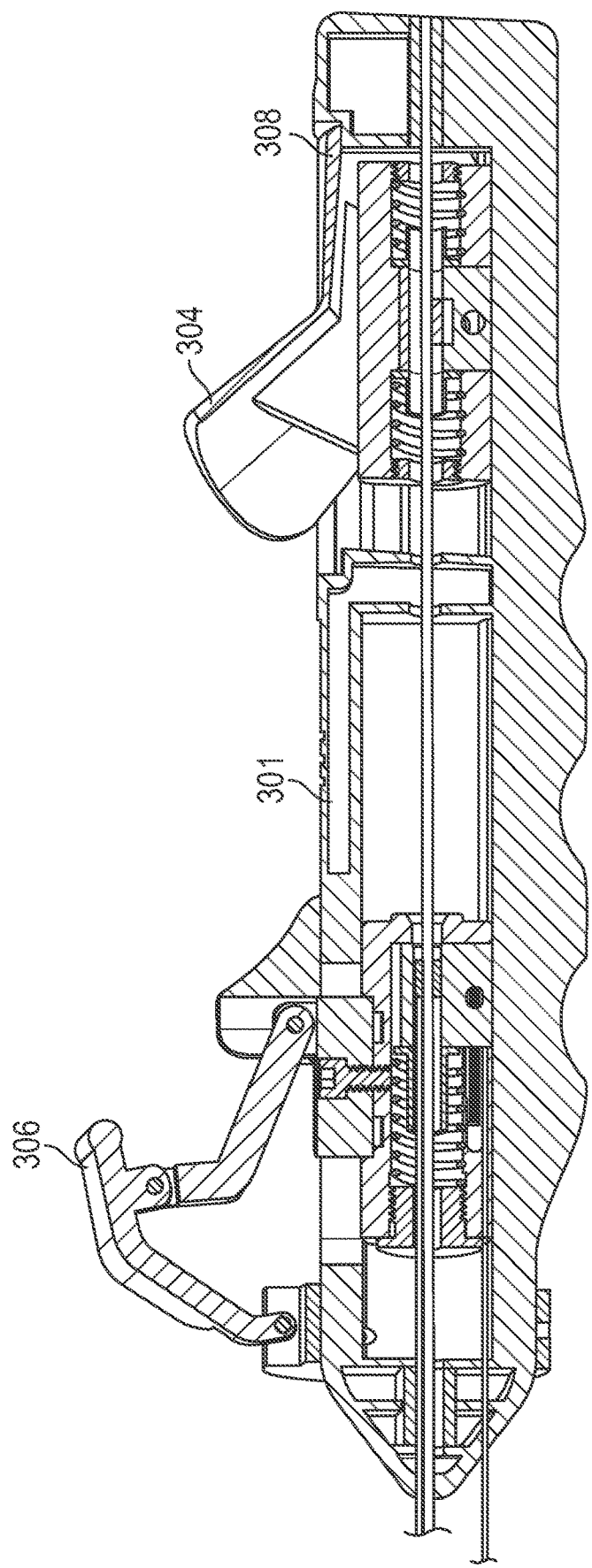
FIG. 20 depicts a cross-sectional view of a handle 301.
Figure 21:
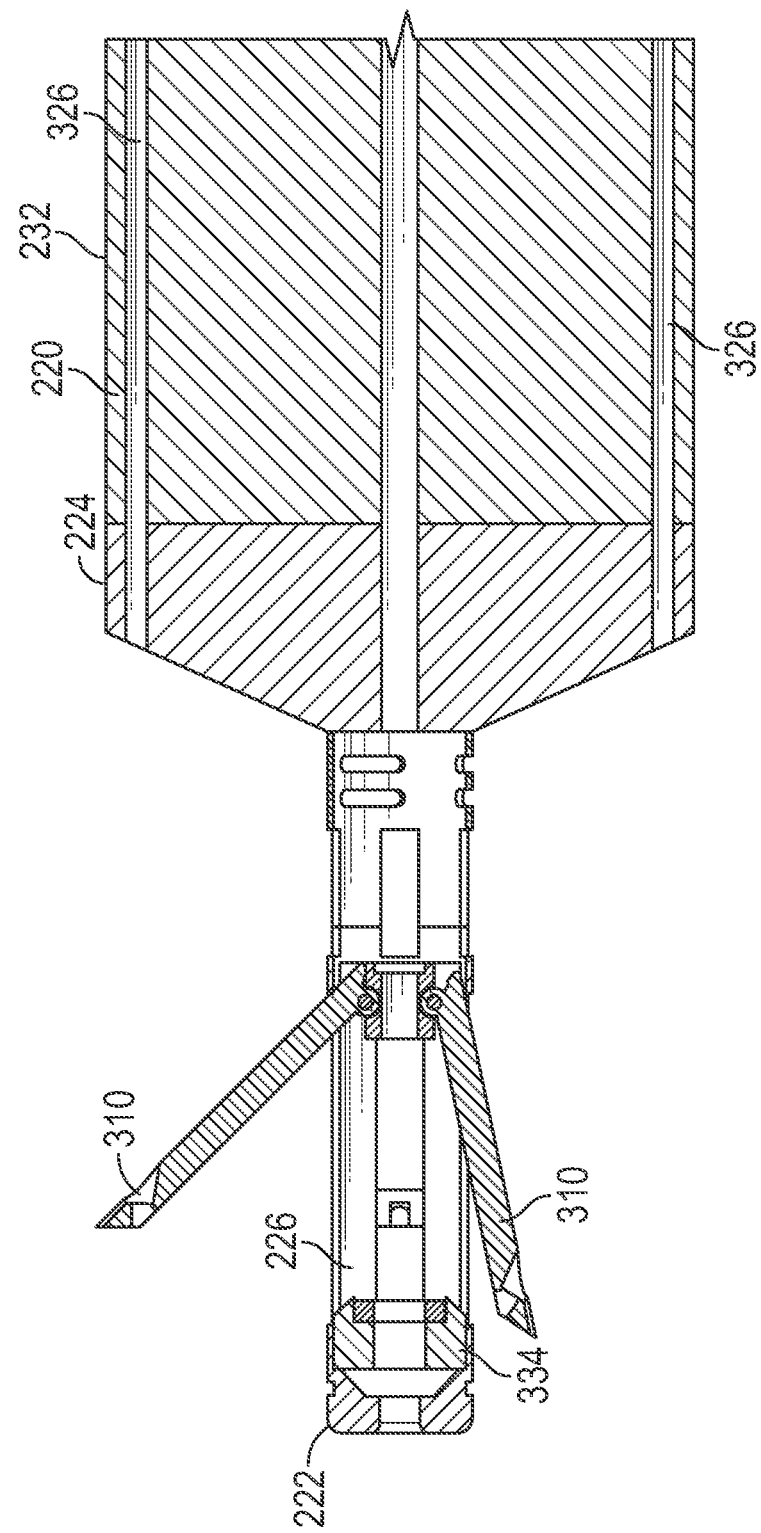
FIG. 21 depicts a cross-sectional view of a distal portion of the suturing device 300 showing one of the arms 310 and one of the needles 320 in an extended position.

FIG. 20 depicts a cross-sectional view of the handle 301 showing the internal components thereof. FIG. 21 depicts a cross-sectional view of the distal end of the suturing device 101 showing the internal components of the elongate body 232, the needle sheath 224, the arm sheath 226 and the distal tip 222 with the suture arms 310 and one of the needles 320 in the extended position. As described herein, the actuator 304 can be actuated to cause one or more of the arms 310 to deploy from the retracted position to the extended position. In some embodiments, actuator 304 can be actuated to deploy each arm 310 at the same time. In some embodiments, individual arms 310 can be actuated. Actuator 306 can be actuated to deploy one or more of the needles 320 from the retracted position to the extended position. In some embodiments, actuator 306 can be actuated to deploy each needle 320 at the same time. In some embodiments, individual needles 320 can be actuated. The actuator 306 can further be manipulated to cause retraction of one or more of the needles 320. In some embodiments, the actuator 306 is configured to cause movement of one or more of the elongate body 232 and the needle sheath 224 in addition to the needles 320. The elongate body 332 and/or needle sheath 224 may translate relative to the arm sheath 226 and distal tip 222. In some embodiments, the actuator 306 can manipulated to cause movement of the needles 320, elongate body 232, and needle sheath 224 together in a proximal-to-distal direction. Upon contact with a surface providing resistance, the elongate body 232 and needle sheath 224 may cease movement while the needles 320 continue to move in the proximal-to-distal direction into the surface contacted by the needle sheath 224. The actuator 306 can further be manipulated to cause retraction of the needles 320, needle sheath 224 and elongate body 232. When the needles 320 are positioned within a surface, the actuator 306 can be manipulated to cause retraction of the needles 320 until the distal ends of the needles 320 retract out of the surface and into the needle sheath 224. The needles 320, needle sheath 224, and elongate body 232 may then all retract in the distal-to-proximal direction. The actuator 308 can be actuated to retract one or more of the arms 310 from the extended position to the retracted position. In some embodiments, actuator 308 can be actuated to retract each arm 310 at the same time. In some embodiments, individual arms 310 can be retracted.

Figure 23A:
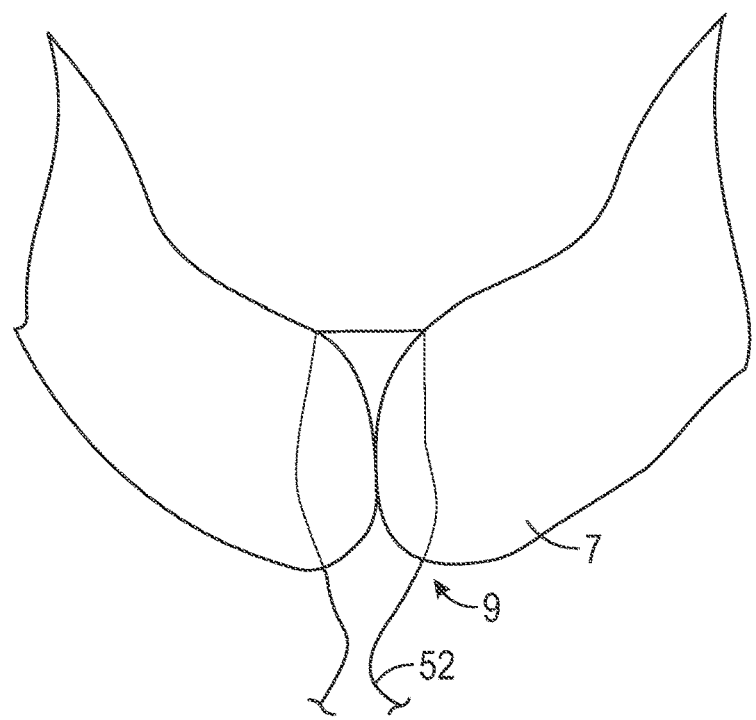
FIG. 23A depicts the suture 52 closing a transapical opening.

FIGS. 22 and 23 illustrate an embodiment of a method of closing a transapical opening using the suturing device 300 of FIGS. 14-21. The suturing device 300 can be introduced through the opening 9 near the apex 7. As indicated above, the suturing device 300 can be introduced into the opening with or without the aid of a guidewire 10 that may pass through a lumen of the elongate body 232 and the distal tip 222. The suturing device 300 can be positioned through the opening a sufficient distance to permit the arms 310 to be deployed within the ventricle 6 of the heart without damage to the surrounding tissue. With the arms 310 deployed, the device 300 can be retracted to cause the arms 310 to engage the heart internal wall tissue surrounding the opening 9. The arms 110 can then be deployed within the ventricle 6. While maintaining the arms 310 in engagement with the heart internal wall tissue, the elongate body 232, needle sheath 224, and needles 320 can be extended in a proximal to distal direction towards the exterior heart wall tissue surrounding the apex. After the needle sheath 224 contacts the exterior heart wall tissue, the needle sheath 224 and elongate body 232 may cease movement while the needles 320 extend from the needle apertures 322 in a proximal-to-distal direction into the heart wall tissue along an axis parallel to a longitudinal axis of the elongate body 232. FIG. 22 shows two of the needles 320 extended through the heart wall tissue adjacent to the opening 9 and to the suture clasps 314 or beyond the suture clasps 314. The needle sheath 224 is shown as transparent in FIG. 22 to illustrate the positioning of the needle within the needle sheath 224. After extending to the suture clasps 314, the needles 320 can snatch the end portions of a suture 52 from the arms 310. For example, the needles 320 can be retracted to snatch the end portions of the suture 52. The suture can be withdrawn through the heart tissue as the needles 320 are retracted back into the needle sheath 224 and elongate body 232, and further as the needles 320, sheath 224, and elongate body 232 are retracted in a distal-to-proximal direction away from the distal tip 222. The arms 310 can then be retracted and the entire suturing device 300 can be withdrawn. The suture can be removed from the device and pulled through the heart tissue to result in the configuration as shown in FIG. 23A, where the suture extends across the transapical opening along an inner surface of the left ventricle and exits the heart from exterior heart wall tissue. Placing the suture along the inner surface of the left ventricle advantageously provides closure to the transapical opening from within the left ventricle.

Figure 23B:
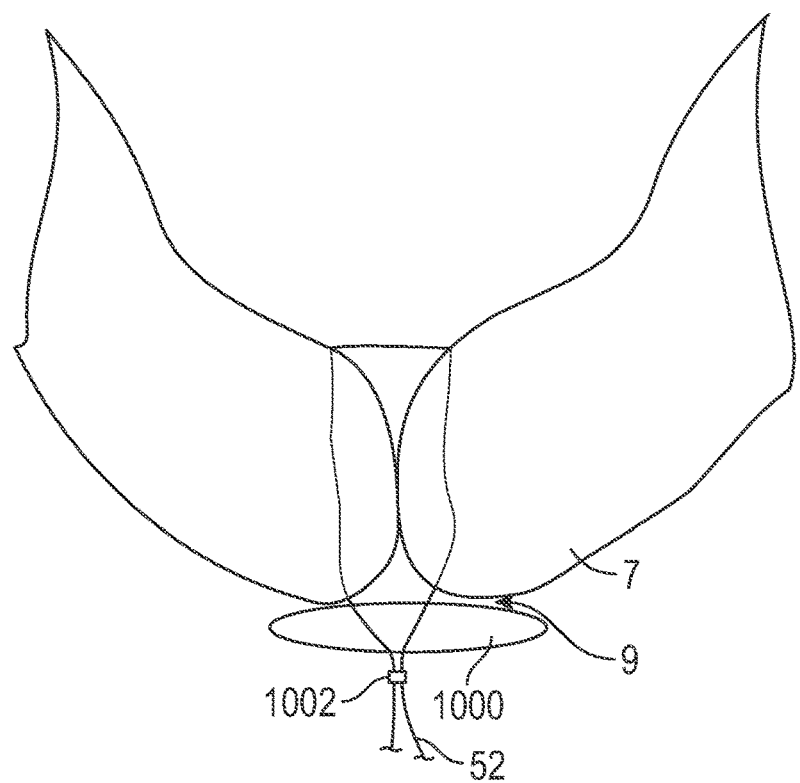
FIG. 23B depicts the suture 52 closing a transapical opening and a pledget 1000.

After the suture 52 has been placed, the suture ends can be tied together or a knot can be placed to close the opening 9, as shown in FIG. 23B. In some embodiments, the placed suture 52 may be an initial suture that is used to then guide an additional suture through the sutured tissue. In such embodiments, the initial suture is removed from the patient and the additional suture is used to draw the opening closed.

FIG. 23 further illustrates placement of a pledget 1000 adjacent the outside surface of the tissue, for example the outside surface of the heart adjacent a sutured transapical opening, to absorb bodily fluid, e.g. blood, adjacent the opening. The pledget can be delivered over suture portions extending away from the opening, and as illustrated, may be deployed with a knot 1002 that secures the suture 52 in closing the transapical opening 9. In another embodiment, the knot 1002 can be placed adjacent the outside surface of the heart, and the pledget 1000 placed over the knot, to provide for readily accessible removal of the temporary placement of the pledget 1000 adjacent the opening 9. Placement of multiple sutures 52 at the opening 9 can provide increased securement of the pledget adjacent the opening 9. In another embodiment, a knot 1002 can be applied both at the heart outer surface wall and on the outer surface of the pledget 1000.

In some embodiments, the two suture arms 310 shown in FIG. 22 hold opposite ends of the suture 52. Although only two needles 320 and arms 310 are shown together in the extended position in FIG. 22, one of skill in the art would understand that two additional arms 310 can be deployed to hold the ends of a second suture, which can be grasped by two additional needles 320. The first pair of suture arms 310 holding opposite ends of the first suture can be diametrically opposed to one another. The second pair of suture arms 310 holding the ends of the second suture can also be diametrically opposed to one another. The four suture arms 310 forming the first pair and second pair of suture arms 310 can be arranged symmetrically about the outer diameter of the arm sheath 226. In some embodiments, the first suture 52 may cross over or under the second suture when extended across the transapical opening 9.

Although the device 300 can be used for suturing transapical openings of the heart, the suturing device 300 can be used to suture other tissues such as, by way of example, a patent ductus arteriosus, a patent foramen *ovale* (PFO), a heart defect, a puncture wound, and the like.

In any of the above-described methods, suture(s) can be placed through the tissue near the opening before or after performing another procedure or procedures through the opening. In some embodiments suture(s) can be placed both before and after performing one or more other procedures.

It is envisioned that the suturing devices and methods described herein can be used to close or reduce a variety of tissue openings, lumens, hollow organs or natural or surgically created passageways in the body. These include, but are not limited to, arterial openings or other blood vessel openings, septal defects, patent foramen *ovale*, and heart valves. The devices and methods can also apply multiple sutures or other pieces of material across the opening simultaneously.

From the foregoing description, it will be appreciated that inventive suturing devices and methods are disclosed. While several components, techniques and aspects have been described with a certain degree of particularity, it is manifest that many changes can be made in the specific designs, constructions and methodology herein above described without departing from the spirit and scope of this disclosure.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include, certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount.

Some embodiments have been described in connection with the accompanying drawings. The figures are not drawn to scale, since dimensions and proportions other than what are shown are contemplated and are within the scope of the disclosed inventions. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

While a number of embodiments and variations thereof have been described in detail, other modifications and methods of using the same will be apparent to those of skill in the art. Accordingly, it should be understood that various applications, modifications, materials, and substitutions can be made of equivalents without departing from the unique and inventive disclosure herein or the scope of the claims as presented now or in the future.

What is claimed is:

1. A suturing device for closing a transapical opening extending through a wall of the heart between inner and outer surfaces of the heart, comprising:

an elongate housing having a proximal end and a distal end configured to be delivered through the transapical opening into a chamber of the heart, the elongate housing comprising a needle-receiving portion and an arm-receiving portion;

a handle at the proximal end of the elongate housing configured to be manipulated from outside of the heart;

a plurality of arms arranged about an outer diameter of the arm-receiving portion of the elongate housing in a retracted position, the arm-receiving portion being distal to the needle-receiving portion when the arms are in the retracted position, the arms being extendable from the arm-receiving portion from the retracted position within the arm-receiving portion to an extended position when the arm-receiving portion is located within the chamber of the heart, wherein each arm is associated with an arm aperture within the arm-receiving portion, wherein a proximal end of each arm is positioned at a proximal end of the respective arm aperture associated with the arm in the retracted position, wherein the proximal end of each arm is configured to move distally within the respective arm aperture associated with the arm from the proximal end of the respective arm aperture to a distal end of the respective arm aperture as the arm moves from the retracted position to the extended position, wherein the arms in the extended position point distally and form an acute angle with a longitudinal axis of the elongate housing, each arm configured to hold a suture portion a distance away from the outer diameter of the arm-receiving portion at or near a distal end of the arm;

a plurality of needles slidably received in the needle-receiving portion of the elongate housing, the needle-receiving portion having a larger cross-sectional dimension than the arm-receiving portion and having a distal end proximal to the arm-receiving portion, each needle being associated with a needle lumen extending at least partially along the length of the elongate housing and at least partially along the length of the needle-receiving portion, each needle further being associated with a needle aperture at the distal end of the needle-receiving portion, wherein each needle is movable in a proximal-to-distal direction along the longitudinal axis of the elongate housing along the respective needle lumen associated with the needle and out of the distal end of the needle-receiving portion through the respective needle aperture associated with the needle to pass through heart tissue into engagement with the suture portion held by one of the arms when the plurality of arms are in the extended position, each of the needles being slidable parallel to each other as the needles move in the proximal-to-distal direction, the needles further being retractable away from the arms back through the heart tissue to draw the suture portions through the heart tissue;

wherein the arms, needle lumens, and needle apertures are configured such that the needle apertures are located outside of the heart and face the outer surface of the heart when the arm-receiving portion is positioned within the chamber of the heart and such that the needles are moveable from outside of the heart through the outer surface of the heart, through the heart tissue and penetrate through the inner surface of the heart radially outward of the transapical opening when the arms are extended inside the chamber of the heart.

2. The suturing device of claim 1, wherein the plurality of arms comprises a first arm and a second arm diametrically opposed from one another.

3. The suturing device of claim 2, wherein the plurality of arms comprises a third arm and a fourth arm diametrically opposed from one another, wherein the first, second, third, and fourth arms are arranged symmetrically about the outer diameter of the arm-receiving portion.

4. The suturing device of claim 3, wherein the first arm and the second arm are configured to hold suture portions of a first suture and the third and fourth arm are configured to hold suture portions of a second suture.

5. The suturing device of claim 1, further comprising a spreading member having a plurality of ramps positioned near a distal end of the arm-receiving portion, each ramp comprising an angled surface extending away from the longitudinal axis of the elongate housing and being positioned to engage the distal end of one of the plurality of arms when the proximal ends of the arms move distally within the arm apertures.

6. The suturing device of claim 1, wherein each needle further comprises a needle hook configured to engage the suture portion held in one of the arms.

7. The suturing device of claim 1, wherein each needle comprises a proximal section having a first diameter and a distal section having a second diameter, the second diameter being smaller than the first diameter.

8. The suturing device of claim 1, further comprising:
a first actuator configured to extend the arms from the retracted position to the extended position;
a second actuator configured to adjust the needles between a retracted position and an extended position; and
a third actuator configured to retract the arms from the extended position to the retracted position.

9. A method for closing a transapical opening in a wall of the heart, comprising:
advancing a suturing device at least partially through the transapical opening, the suturing device comprising:
an elongate body having a proximal end and a distal end and a handle at the proximal end of the elongate body configured to be manipulated from outside of the heart;
a needle sheath positioned distal to the distal end of the elongate body;
an arm sheath having a diameter less than a diameter of the elongate body;
a tip positioned distal to a distal end of the arm sheath and configured to be delivered through the transapical opening and into a ventricle of the heart;
four arms proximal to the tip arranged symmetrically about an outer diameter of the arm sheath in a retracted position, the arm sheath being distal to the needle sheath when the arms are in the retracted position, each arm configured to hold a suture portion a distance away from the outer diameter of the arm sheath at or near a distal end of the arm, the arms being extendable from said arm sheath from the retracted position to an extended position, wherein each arm is associated with an arm aperture within the arm sheath, wherein a proximal end of each arm is positioned at a proximal end of the respective arm aperture associated with the arm in the retracted position, wherein the proximal end of each arm is configured to move distally within the respective arm aperture associated with the arm from the proximal end of the respective arm aperture to a distal end of the respective arm aperture as the arm moves from the retracted position to the extended position, wherein the arms in the extended position point distally and form an acute angle with a longitudinal axis of the elongate body; and four needles slidably housed in said elongate body, each needle being associated with a needle lumen extending at least partially along the length of the elongate body and at least partially along the length of the needle sheath, each needle further being associated with a needle aperture at the distal end of the needle sheath, wherein each needle is movable in a proximal-to-distal direction along the longitudinal axis of the elongate body along the respective needle lumen associated with the needle and out of the distal end of the needle sheath through the respective needle aperture associated with the needle to pass through heart tissue into engagement with the suture portion held by one of the arms, each of the needles being slidable parallel to each other as the needles move in the proximal-to-distal direction, the needles further being retractable away from the arms back through the heart tissue to draw the suture portions through the heart tissue;

positioning the suturing device such that the four arms are positioned within the ventricle of the heart and a distal end of the needle sheath is exterior to the wall of the heart;

extending the arms from the suturing device from the retracted position to the extended position in the ventricle of the heart;

extending the needles through the wall of the heart in a proximal-to-distal direction along an axis parallel to the longitudinal axis of the elongate body into engagement with the suture portions held by the arms;

retracting the needles through the wall of the heart to draw the suture portions through the wall of the heart;

retracting the arms from the extended position to the retracted position;

withdrawing the suturing device from the transapical opening; and closing the transapical opening with the suture portions.

10. The method of claim 9, wherein each needle further comprises a needle hook configured to engage the suture portion held in one of the arms.

11. The method of claim 9, wherein each needle comprises a proximal section having a first diameter and a distal section having a second diameter, the second diameter being smaller than the first diameter.

12. The method of claim 9, wherein the suturing device comprises:
a first actuator configured to extend the arms from the retracted position to the extended position;
a second actuator configured to adjust the needles between the retracted position and extended position; and
a third actuator configured to retract the arms from the extended position to the retracted position.

13. The method of claim 9, further comprising retracting the suturing device so that the extended arms engage heart internal wall tissue prior to extending the needles.

14. The method of claim 13, further comprising extending the elongate body, needle sheath, and needles in a proximal-to-distal direction towards the heart until the needle sheath contacts an exterior surface of the heart while the arms engage the heart internal wall tissue.

15. The method of claim 14, wherein extending the needles through the wall of the heart, comprises extending the needles through the needle apertures and into the wall of the heart after the needle sheath contacts the exterior surface of the heart.

16. The method of claim 15, wherein the suturing device comprises a single actuator configured to extend the elongate body, needle sheath, and needles in a proximal-to-distal direction towards the heart.

17. The method of claim 16, further comprising retracting the needles, needle sheath, and elongate body simultaneously using the single actuator.

18. The method of claim 9, wherein a first pair of the four arms hold suture ends of a first suture and a second pair of the four arms hold suture ends of a second suture.

* * * * *

UNITED STATES PATENT AND TRADEMARK OFFICE
CERTIFICATE OF CORRECTION

| | | |
|---|---|---|
| PATENT NO. | : 11,839,370 B2 | Page 1 of 1 |
| APPLICATION NO. | : 16/624611 | |
| DATED | : December 12, 2023 | |
| INVENTOR(S) | : Anthony A. Nobles | |

It is certified that error appears in the above-identified patent and that said Letters Patent is hereby corrected as shown below:

In the Specification

On Column 1, Line 10: Delete "Jun. 9," and insert -- Jun. 19, --.

On Column 14, Line 39: Delete "450" and insert -- 45° --.

Signed and Sealed this
Twentieth Day of February, 2024

*Katherine Kelly Vidal*

Katherine Kelly Vidal
*Director of the United States Patent and Trademark Office*